United States Patent
Meyer et al.

(10) Patent No.: US 11,236,150 B2
(45) Date of Patent: Feb. 1, 2022

(54) HETERO-DIMERIC MULTI-SPECIFIC ANTIBODY FORMAT

(71) Applicant: NUMAB THERAPEUTICS AG, Wadenswil (CH)

(72) Inventors: Sebastian Meyer, Eggenwil (CH); David Urech, Jona (CH)

(73) Assignee: NUMAB THERAPEUTICS AG, Wädenswil (CH)

( * ) Notice: Subject to any disclaimer, the term of this patent is extended or adjusted under 35 U.S.C. 154(b) by 297 days.

(21) Appl. No.: 15/736,747

(22) PCT Filed: Jun. 15, 2016

(86) PCT No.: PCT/EP2016/001002
§ 371 (c)(1),
(2) Date: Dec. 14, 2017

(87) PCT Pub. No.: WO2016/202457
PCT Pub. Date: Dec. 22, 2016

(65) Prior Publication Data
US 2018/0355024 A1    Dec. 13, 2018

(30) Foreign Application Priority Data

Jun. 15, 2015 (EP) .................................... 15001758

(51) Int. Cl.
*C07K 16/00* (2006.01)
*C07K 16/24* (2006.01)
*C07K 16/28* (2006.01)

(52) U.S. Cl.
CPC ............ *C07K 16/00* (2013.01); *C07K 16/241* (2013.01); *C07K 16/2809* (2013.01); *C07K 16/2866* (2013.01); *C07K 2317/31* (2013.01); *C07K 2317/60* (2013.01); *C07K 2317/62* (2013.01); *C07K 2317/622* (2013.01); *C07K 2317/626* (2013.01)

(58) Field of Classification Search
CPC ..................................................... C07K 46/00
USPC ...................................................... 424/136.1
See application file for complete search history.

(56) References Cited

U.S. PATENT DOCUMENTS

2005/0003403 A1* 1/2005 Rossi ................. C07K 16/3007
435/6.16

FOREIGN PATENT DOCUMENTS

| EP | 3131928 B1 | 11/2019 |
|----|----|----|
| WO | 2010/132872 | 11/2010 |
| WO | 2011/086091 | 7/2011 |
| WO | 2012/088290 | 6/2012 |
| WO | 2012/135345 | 10/2012 |
| WO | 2013/003652 | 1/2013 |
| WO | 2014/022540 | 2/2014 |
| WO | 2014/122529 | 8/2014 |
| WO | 2014/180577 | 11/2014 |
| WO | 2014/180754 | 11/2014 |
| WO | 2015/158636 A1 | 10/2015 |
| WO | 2017/064221 A1 | 4/2017 |

OTHER PUBLICATIONS

Feng et al (Am J Transl Res, 2011, 3(3): 269-274).*
Roskopf et al (Oncotarget, 2014, 5(15): 6466-6483).*
International Search Report dated Aug. 22, 2016 in PCT/EP2016/001002 (6 pages).
Written Opinion dated Aug. 22, 2016 in PCT/EP2016/001002 (6 pages).
Strawman Opposition Filing, Apr. 30, 2021.
Patentee Test Report Filing, Apr. 30, 2021.
Patentee Response Filing, Apr. 30, 2121.
Opposition Test Report Filing, Apr. 30, 2021.

* cited by examiner

*Primary Examiner* — Sean E Aeder
(74) *Attorney, Agent, or Firm* — Prismatic Law Group, PLLC

(57) ABSTRACT

The invention relates to a novel hetero-dimeric multi-specific format of multiple antibody variable domains comprising a core of two split variable domain pairs wherein both variable light domains and the two cognate variable heavy domains are positioned in tandem on two separate protein chains, respectively.

17 Claims, 17 Drawing Sheets
Specification includes a Sequence Listing.

A:

B:

A:

B:

A:

B:

SEQUENCE LISTING

```
<160> NUMBER OF SEQ ID NOS: 4

<210> SEQ ID NO 1
<211> LENGTH: 10
<212> TYPE: PRT
<213> ORGANISM: artificial
<220> FEATURE:
<223> OTHER INFORMATION: artificial linker

<400> SEQUENCE: 1

Gly Gly Gly Gly Ser Gly Gly Gly Gly Ser
1               5                   10

<210> SEQ ID NO 2
<211> LENGTH: 15
<212> TYPE: PRT
<213> ORGANISM: artificial
<220> FEATURE:
<223> OTHER INFORMATION: artificial linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 6
<212> TYPE: PRT
<213> ORGANISM: artificial
<220> FEATURE:
<223> OTHER INFORMATION: artificial linker

<400> SEQUENCE: 3

Gly Gly Ser Gly Gly Ser
1               5

<210> SEQ ID NO 4
```

```
<211> LENGTH: 8
<212> TYPE: PRT
<213> ORGANISM: artificial
<220> FEATURE:
<223> OTHER INFORMATION: artificial linker

<400> SEQUENCE: 4

Gly Gly Gly Ser Gly Gly Gly Ser
1               5
```

HETERO-DIMERIC MULTI-SPECIFIC ANTIBODY FORMAT

The present invention is filed under 35 U.S.C. § 371 as the U.S. national phase of International Patent Application No. PCT/EP2016/001002, filed Jun. 15, 2016, which designated the United States and which claims priority to European Patent Application No. 15001758.0 filed Jun. 15, 2015, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Dec. 14, 2017, is named N_0009_USNP_SeqListing.txt and is 2 kilobytes in size.

FIELD OF THE INVENTION

This invention relates to novel hetero-dimeric multi-specific format of multiple antibody variable domains comprising a core of two split variable domain pairs wherein both variable light domains and the two cognate variable heavy domains are positioned in tandem on two separate protein chains, respectively.

BACKGROUND OF THE INVENTION

In the past forty years since the development of the first monoclonal antibodies [R17], antibodies have become an increasingly important class of biomolecules for research, diagnostic and therapeutic purposes.

Antibodies, as therapeutic agents, are evolving towards more rationally designed functionalities thus improving and expanding their inherent properties. Examples include the optimization of effector functions by glycoengineering [R18], specific localization like the transfer over the blood brain barrier [R19], or tuned half-life by e.g. increased binding to FcRn [R20].

A complementary approach of antibody functionalization is the combination of different target specificities in one molecule to generate bi- or multispecific antibodies or antibody fragments, thus allowing alternative mechanisms of action, like the retargeting of T cells, as exemplified by bispecific antibody Blinatumomab or the trispecific antibody Catumaxomab.

Despite the large number of different multispecific antibody formats that have been developed so far [R21], the current repertoire of bi- and multispecific antibody formats still leaves the industry with considerable technical challenges and little flexibility with only few formats that allow for tri- and multi-specific binding and even less formats supporting the formation of hetero-dimeric proteins.

Different multi-specific formats have been presented in the past. Conceptually these formats can be grouped into three categories: a) single-chain multi-specific formats, in which the different target binding domains are all located on one single protein chain, expressed from a single gene, b) homo-bi- and homo-multimeric formats, in which the different target-binding domains are located on identical protein chains that are assembled by the use of a multimerization domain resulting in bi-/multi-valent and optionally also multi-specific complexes, and c) hetero-dimeric formats in which the target-binding domains are located on different protein chains, and the assembly of the two protein chains is driven by a hetero-dimerization domain.

Hetero-dimeric multi-specific formats in principle offer the advantage that binding domains with different specificities and affinities can easily be tested in various combinations by simple permutation of the two hetero-dimerizing protein chains, thereby allowing for the screening for optimal combinations of specificities and affinities directly in the final format without the need for tedious cloning.

Such screening in the final product format is required in cases where the binding properties and/or potencies of the various domains need to be carefully matched to each other to achieve optimal potency of the bi-specific protein and at the same time minimize the risk for unspecific effects. In the clinical situation this would translate to optimal efficacy at minimal risk of adverse effects. Situations, where such optimal combinations are required, may for example be the concomitant blockade of two disease-driving cytokines that are produced in the course of the disease in different concentrations. In this situation, the therapeutic bi-specific protein should allow to effectively block both cytokines at one and the same therapeutic dose.

Another example, where the characteristics of the target-binding domains of a multi-specific molecule must be coordinated, is the therapy of cancer with a cytotoxic antibody targeting two cell surface targets on the tumor cells. While the two cell surface targets of the antibody in this situation may be co-expressed exclusively on cancer cells, they may be expressed individually in a variety of healthy tissues. In order to achieve best efficacy at lowest risk for adverse side effects in tumor therapy, the cytotoxic antibody should bind to a cell preferentially, when both targets are co-expressed, but should not bind to tissues expressing only one of the two targets. To achieve this, the affinities of the two target-binding domains need to be tuned such that on one hand the affinities of the individual domains to their target are too weak to result in cell lysis, and on the other hand the cooperative avidity resulting from concomitant binding of the bi-specific molecule to both targets on a cancer cell is sufficient to induce cell lysis. Due to geometrical constraints resulting from the simultaneous binding to different macromolecules immobilized on the cell surface, the combination of domains to achieve maximal cooperative binding is not only a function of affinities, but also of epitopes and may only be identified by testing different domain combinations in the actual product format.

The native IgG type antibody can be considered a homo-dimeric format.

In order to increase the number of specificities of the homo-dimeric antibody format employing the classic IgG architecture as a scaffold, additional binding moieties, such as single-chain Fvs [R15], Fvs [R16], single domains [e.g. Nanobodies: Huang et al., Expert Rev Mol Diagn. 10 (2010):777-85] or alternative scaffolds [e.g. Fynomers: Schlatter et al., MAbs. 4 (2012) 497-508] can be appended, either to the amino- or the carboxyl-terminus of both the heavy and the light chain. One advantage of this approach is that bi- to tri-specific constructs can be generated with a conventional IgG as core domain, which allows exploiting most of the manufacturing and modification technologies that have been established for conventional IgGs. Due to the homo-dimeric nature of conventional Fc regions, however, this approach will always result in at least two identical binding domains per molecule and consequently in bivalent binding to a certain target. This may not always be wanted, particularly not (a) if only cooperative binding to two targets shall result in the desired effect, of (b) if the molecular weight shall not be further increased. Furthermore, this approach oftentimes suffered from poor domain stabilities of the appended binding moieties rendering them unsuitable for pharmaceutical development.

The concept of fusing further binding domains to increase specificities can also be applied to Fab fragments [R14] or other antigen-binding fragments of IgGs [R23]. Due to the hetero-dimeric nature of the Fab, consisting of a heavy and a light chain, the Fab fragment can be used as a hetero-dimerization domain. The Fab fragment has for example been used to engineer the so-called Tribody. In this format scFv fragments are fused to the carboxyl-terminus of both the light and the heavy chain of a Fab resulting in a truly hetero-dimeric tri-specific molecule. The light chain-heavy chain association of the Fab is mainly driven by the interaction between CL-CH1, which in addition are connected though a covalent disulfide-bond [R2]. Challenges with this format are (a) the limitation of stability to the least stable component, which will most probably be the appended scFv, and (b) the limitation to maximally three target specificities.

As an approach to solve the limitations of homo-dimeric bi-specific formats, hetero-dimeric IgGs have been introduced [R31]. Simple co-expression of two different mAbs from one cell leads with very low probability to the assembly of hetero-dimeric bi-specific IgGs in which two different heavy chains will pair with each other, and the two different light chains will pair with their corresponding heavy chain [R24]. It will, however, also lead to A) the mismatch of heavy and light chains with different specificities and to B) mixtures of different heavy chain combinations resulting in mono- and bi-specific variants. To address these difficulties several approaches have been undertaken, which create an artificial asymmetry in the molecules. The "knob-into-holes" concept [R3, R4] uses engineering of the heavy chain/heavy chain or heavy chain/light chain interface to drive the association of the co-expressed chains towards the desired configuration. In another approach the CrossMab methodology [R5] allows selective pairing of an engineered light chain/heavy chain pair. A drawback of these methodologies is that the any residual fraction of mismatched molecules is very difficult to separate from the product. Therefore other techniques focus on the separation problem by engineering differential binding properties for the mono- and bispecific binders [R22] and on the other hand tolerate the loss in yield caused by the stochastic distribution of variants.

A further limitation of the IgG-based hetero-dimeric formats is that they all must comprise an Fc effector domain. A format in which hetero-dimerization would be driven by target binding domains directed to any target of choice would allow increasing the number of specificities/functionalities at the same or lower molecular weight. Molecules with lower molecular weights penetrate more efficiently into target tissues (e.g. solid cancers) and thus hold the promise for improved efficacy at the same or lower dose.

Such small formats could still be engineered to have a serum half-life comparable to that of an IgG simply by adding for example a binding-domain that interacts with serum albumin.

An alternative approach uses non-antibody fusion proteins to confer the desired multispecificity of for example scFv moieties. Examples of such fusion proteins are Dock-and-Lock [R25], barnase-barstar [R26], jun-fos [R27], TNF [R28], or HSA [R29]. These concepts have in common that at least one pair of domains is added that interact in a hetero-dimeric fashion to bring the bi- or multispecific binding domains together. These hetero-dimerization domains are not directly involved in target binding, nevertheless, they increase the molecular weight of the protein—similar to the constant region one (C1) in the Tribody format. Furthermore, they might come with the risk of increased immunogenicity by incorporating non-human epitopes and sequences.

In contrast to the interaction between CL and CH1 discussed above, the association of the paratope-forming VL-VH domains is generally regarded as weak. However, there are several hetero-dimeric antibody fragment concepts that are comprised exclusively of antibody variable domains. Approaches like diabodies [R6], DARTs [R10], and tandabs [R7, R8], amongst others, offer elegant and minimalistic approaches to create homo- and hetero-dimeric bispecific and bi- to tetra-valent assemblies. The most important limitations of these formatting strategies are (a) the addition of further specificities by fusing e.g. an scFv to the amino- or the carboxyl-terminus of either chain of diabodies or DARTs could result in the intra-chain pairing of the variable light and variable heavy domains thereby rendering hetero-dimerization of the two protein chains very challenging, and (b) due to the weak domain interface binding between the variable light and the variable heavy chain often observed in the past, these formats suffered from low monomeric stability and poor producibility, so that further engineering such as the introduction of inter-domain disulfide bonds [R12] to stabilize the VL/VH interface was regarded as being necessary.

Aiming at constructing multi-specific single-chain tandem Fv antibodies, Kipriyanov et al [R30] suggested a design comprising two protein chains, each consisting of two split Fv domains arranged in the order VL-(linker1)-VH-(linker2)-VL-(linker3)-VH. For the construction of hetero-dimeric tetra-specific proteins, the hetero-dimer would consist of two protein chains with the following architecture. Chain 1: VLA-(linker1)-VHA-(linker12)-VLB-(linker13)-VHC, and chain B: VLD-(linker1)-VHD-(linker2)-VLC-(linker3)-VHB, wherein the assembly of FvB and FvC would drive hetero-dimerization of the two chains (see FIG. 10A). In order to prevent intra-chain assembly resulting in a tandem single-chain Fv (scFv2)-like format, and to promote hetero-dimerization of two monomeric protein chains, shortened linkers at positions linker3 of maximally 10 amino acids have been suggested (EP1293514 A1) The proposed organization of the two split variable domains with a linker2 of at least 15 amino acids, however, results in the possibility of the second variable domains to fold back onto N-terminal domains, leading to a single-chain diabody (scDb)-like format consisting of non-matching VH/VL pairs, which in consequence would likely not be able to bind their target. In addition, there is also the potential for the formation of a hetero-dimer in which all variable heavy and light chains on protein chain 1 would pair with the variable light and heavy chains of protein chain 2, respectively, thereby preventing the formation of the terminal scFvs (scFvA and scFvD) and resulting in the pairing of non-cognate variable domains. The tandem scFv (scFv2) or scDb-type byproducts might be the reason for the very high fraction of protein observed at the apparent molecular weight of the non-multimerized protein chains [R30].

In theory the formation of scDb-like structures in the approach described above, could be further reduced by shortening also the second linker (linker2) between the two split variable domains. This would however, limit the flexibility of the construct, which in many cases would negatively impact on the range of accessible epitopes that allow for concomitant binding of two targets. These geometrical constraints are particularly limiting when two membrane proteins shall be bound at the same time.

Additionally, and most importantly however, both monomers might form homodimeric fragments (see FIG. 10B), so that statistically up to two thirds of dimeric products could consists of the two homodimers, while only one third would consist of the desired hetero-dimer.

In summary, there is a well pronounced industry need for hetero-dimeric multi-specific formats that allow for simple permutation and subsequent characterization of different binding domains in the final format. Major challenges with such formats have been (a) the relatively poor efficiency of specific hetero-dimerization resulting in suboptimal production yields, and (b) the necessity to use either non target binding proteins as hetero-dimerization domains or engineered hetero-dimer Fc effector domains that come with poor flexibility in tuning serum half-life and that limit the flexibility in adding novel functionalities without increasing the molecular weight.

Thus, the optimal hetero-dimeric multi-specific format would exclusively consist of target binding domains and would allow for adjusting the geometry of the molecule for example by freely changing the linker lengths between the different binding domains to accommodate the geometrical constraints defined by the interaction partners (targets). The solution to this problem, i.e. the modification of the order of the variable domains on the monomeric chains, has hitherto neither been shown nor suggested in the prior art.

SUMMARY OF THE INVENTION

This invention relates to novel hetero-dimeric multi-specific format of multiple antibody variable domains comprising a core of two split variable domain pairs wherein both variable light domains and two cognate variable heavy domains are positioned in tandem on two separate protein chains, respectively, thereby driving hetero-dimerization of the two protein chains. Up to two additional binding domains, particularly antibody-based binding domains, such as scFv fragments, are fused to the amino- or the carboxyl-terminus of either protein chain, resulting in an up to hexa-specific hetero-dimeric protein.

Thus, in a first aspect the present invention relates to a hetero-dimeric protein comprising a first and a second single-chain protein, wherein said first single-chain protein comprises a first amino acid sequence consisting of (from the N- to the C-terminus):
  (ia) a first VL domain;
  (iia) a first polypeptide linker and
  (iiia) a second VL domain, and
wherein said second single-chain protein comprises a second amino acid sequence consisting of (from the N- to the C-terminus):
  (ib) a first VH domain;
  (iib) a second polypeptide linker and
  (iiib) a second VH domain, and
wherein said first VL domain forms a first cognate pair of variable domains with specificity to a first target antigen with either said first or said second VH domain and said second VL domain forms a second cognate pair of variable domains with specificity to a second target antigen with the other of said VH domains, and wherein at least one of said first or said second single-chain protein further comprises
  (iv) at least one additional domain as third functional domain that is fused via a third polypeptide linker to said first or said second amino acid sequence, wherein, optionally, said hetero-dimeric protein does not comprise a cognate pair of a first and a second immunoglobulin constant domain, wherein said first immunoglobulin constant domain is comprised in said first single-chain protein and wherein said second immunoglobulin constant domain is comprised in said second single-chain protein.

In a second aspect, the present invention relates to one or two nucleic acid sequences encoding said first and a second single-chain proteins.

In a third aspect, the present invention relates to one or two vectors comprising said one or two nucleic acid sequences.

In a fourth aspect, the present invention relates to a host cell or host cells comprising one or two vectors.

In a fourth aspect, the present invention relates to a method for producing the first and second single-chain proteins, or the hetero-dimeric protein, of the present invention, comprising (i) providing a nucleic acid or nucleic acids according to the present invention, or a vector or vectors according to the present invention, expressing said nucleic acid or nucleic acids or said vector or vectors and collecting said first and second single-chain proteins, or said hetero-dimeric protein, from the expression system, or (ii) providing a host cell or host cells of the present invention, culturing said host cell or host cells, and collecting said first and second single-chain proteins, or said hetero-dimeric protein, from the cell culture.

In a fifth aspect, the present invention relates to a pharmaceutical composition comprising the hetero-dimeric protein of the present invention and a pharmaceutically acceptable carrier.

In a sixth aspect, the present invention relates to the hetero-dimeric protein of the present invention for use in the treatment of a disease, particularly a human disease, more particularly a human disease selected from cancer, an inflammatory and an autoimmune disease, wherein at least one of said cognate pairs of VL and VH domains, or of said third, fourth, fifth, or sixth functional domain is able to specifically interact with a target of therapeutic relevance in the corresponding disease.

In a seventh aspect the present invention relates to a method for treating a patient suffering from a disease, particularly a human disease, more particularly a human disease selected from cancer, an inflammatory and an autoimmune disease, comprising administering to a subject an effective amount of the hetero-dimeric protein of the present invention, wherein at least one of said cognate pairs of VL and VH domains, or of said third, fourth, fifth, or sixth functional domain is able to specifically interact with a target of therapeutic relevance in the corresponding disease.

Particular embodiments of the present invention are set forth in the appended dependent claims.

FIGURES

Figure 6A:
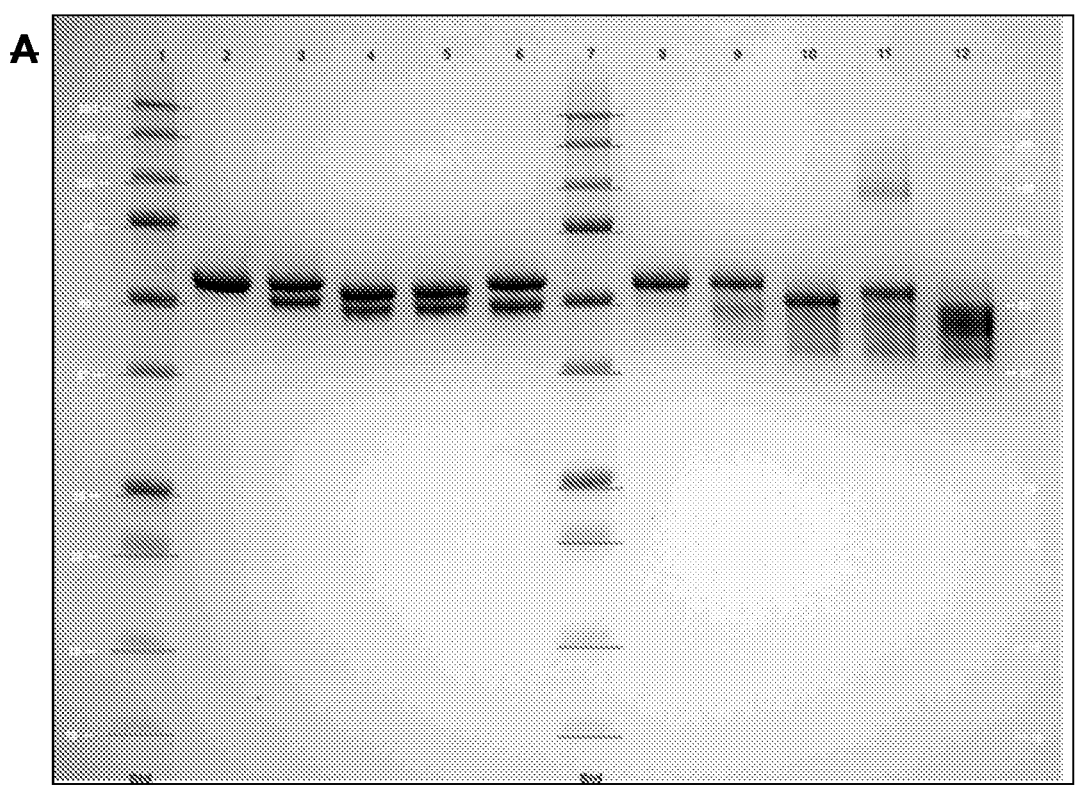
Figure 6B:
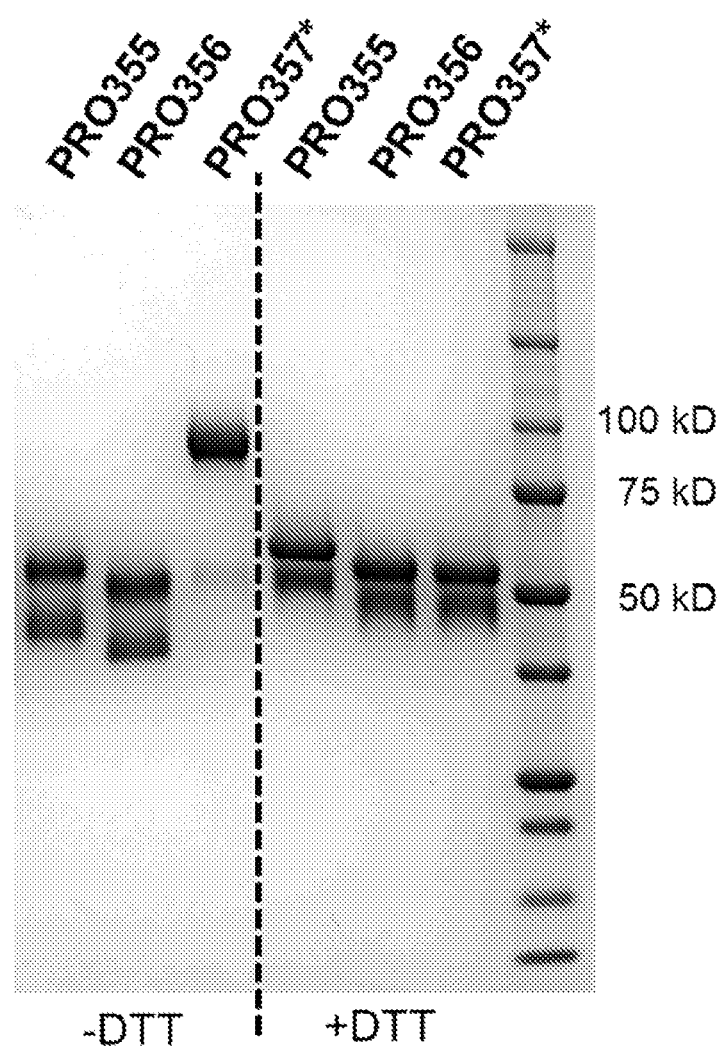
Figure 7:
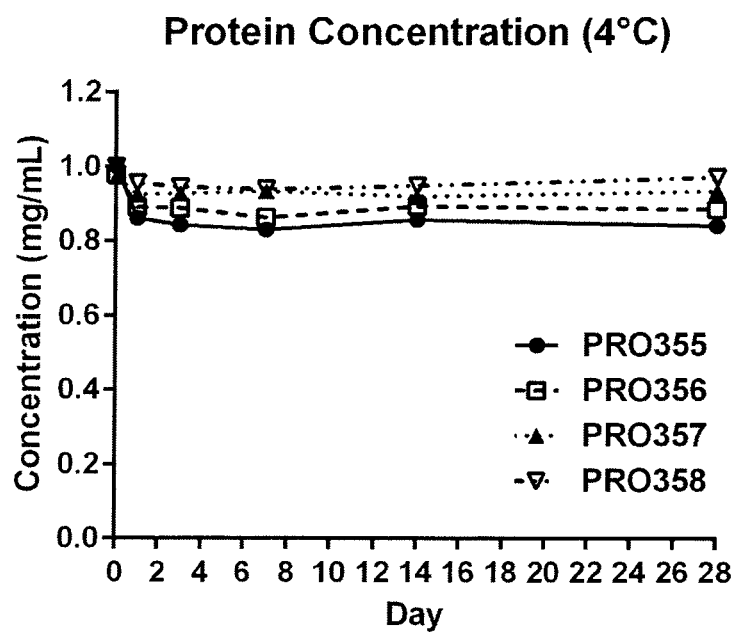
Figure 7:
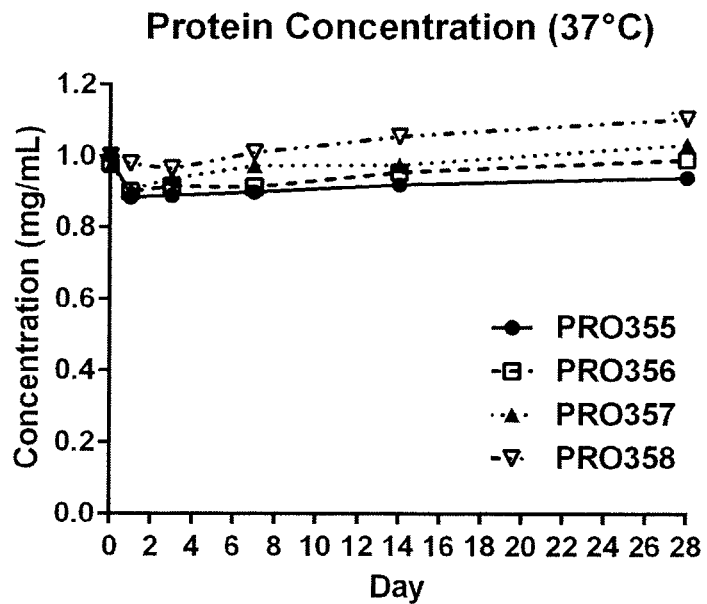

FIG. 6 shows the SDS-PAGE analysis after a 1-step purification: Panel A: PRO356 (Assembly 1): reducing conditions: lane 4; non-reducing conditions: lane 10; PRO357 (Assembly 3): reducing conditions: lane 5; non-reducing conditions: lane 11; PRO358 (Assembly 5) reducing conditions: lane 6; non-reducing conditions: lane 12; PRO355 (Assembly 7) reducing conditions: lane 3; non-reducing conditions: lane 9. Panel B: a repetition of the SDS-PAGE with lower temperature during sample preparation showing pronounced crosslinking of PRO357 (Assembly 3) non-reducing conditions FIG. 7 shows the protein content after 28 d storage at 37° C. (1 g/L) (FIG. 7B) in comparison to storage at 4° C. (FIG. 7A): PRO356 (Assembly 1); PRO357 (Assembly 3); PRO358 (Assembly 5); PRO355 (Assembly 7).

Figure 8:
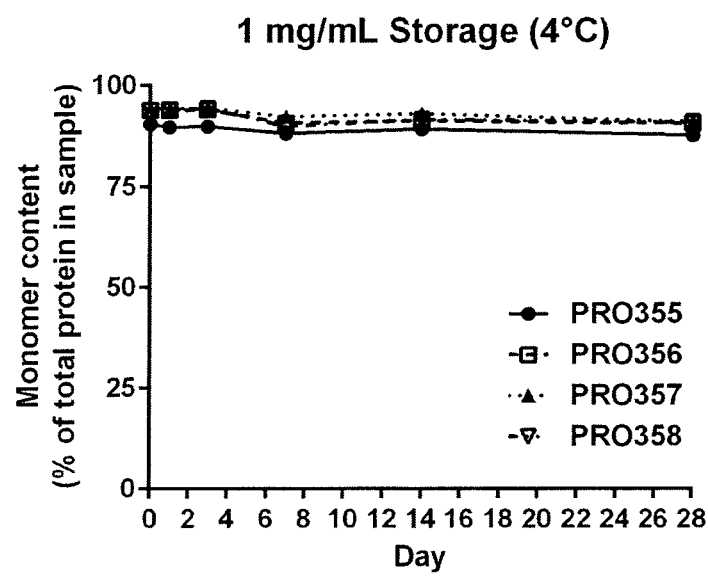
Figure 8:
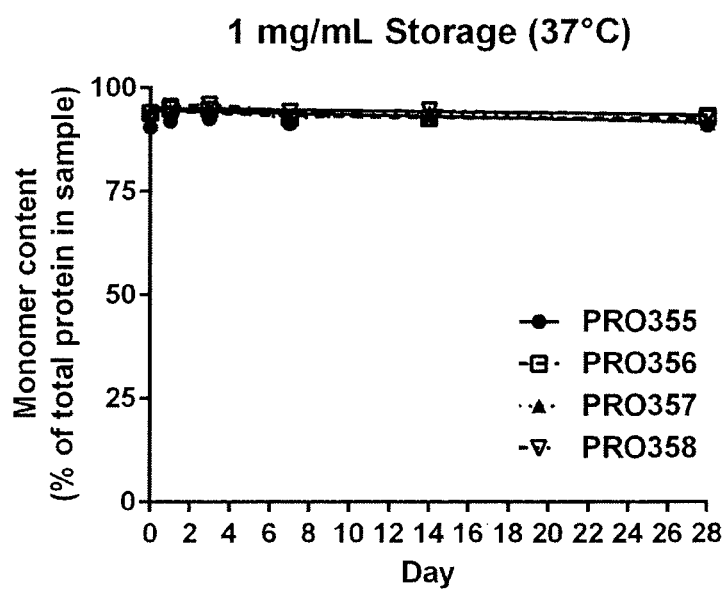

FIG. 8 shows the monomer content after 28 d storage at 37° C. (1 g/L) (FIG. 8B) in comparison to storage at 4° C. (FIG. 8A): PRO356 (Assembly 1); PRO357 (Assembly 3); PRO358 (Assembly 5); PRO355 (Assembly 7).

Figure 9:
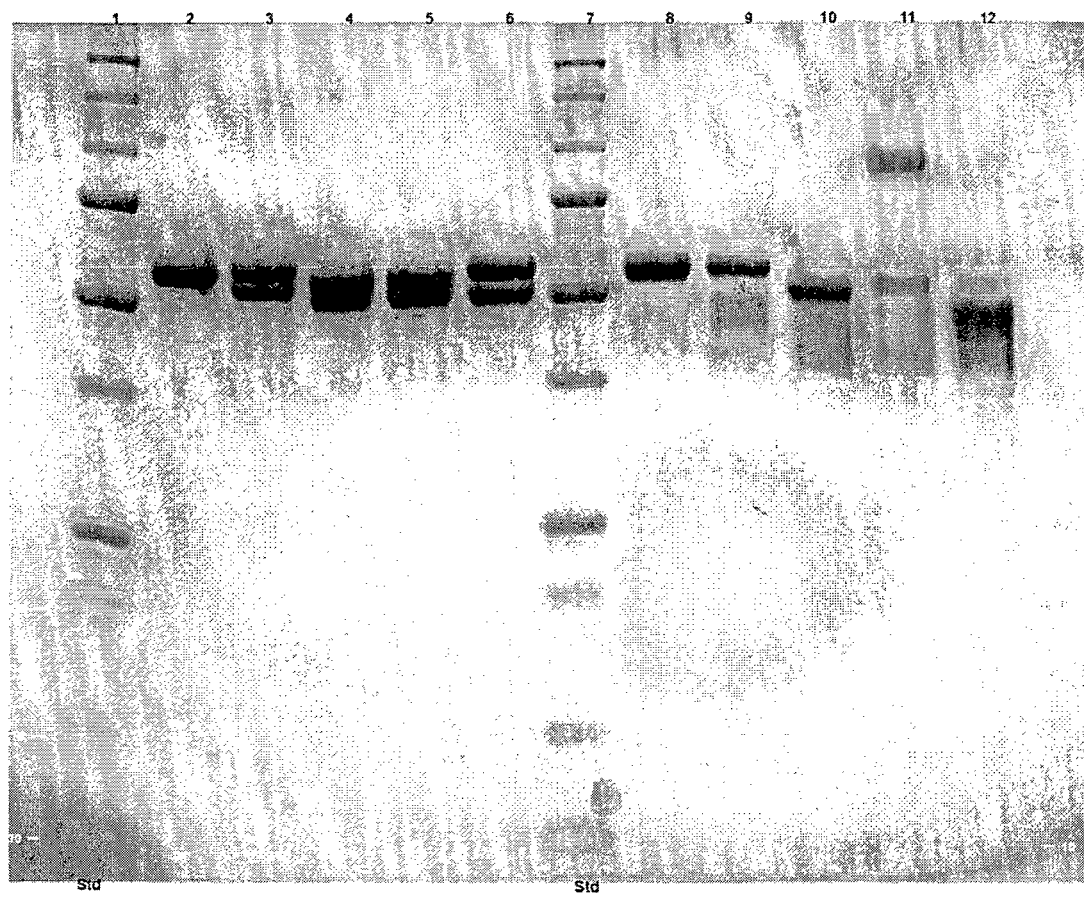

FIG. 9 shows the SDS-PAGE analysis of the stability samples after incubation for four weeks at 37° C.: PRO356 (Assembly 1): reducing conditions: lane 4; non-reducing conditions: lane 10; PRO357 (Assembly 3): reducing conditions: lane 5; non-reducing conditions: lane 11; PRO358 (Assembly 5) reducing conditions: lane 6; non-reducing conditions: lane 12; PRO355 (Assembly 7) reducing conditions: lane 3; non-reducing conditions: lane 9.

Figure 10:
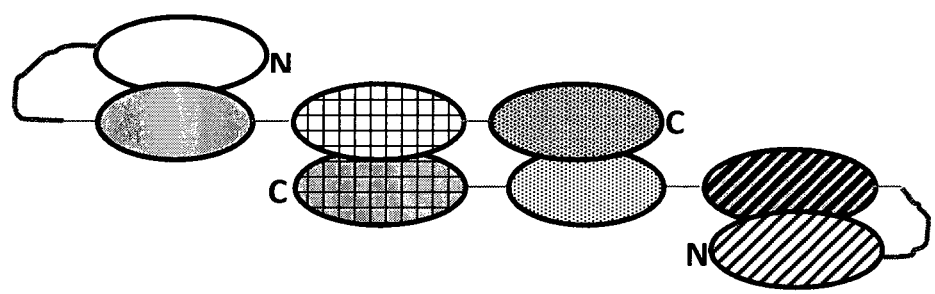
Figure 10:
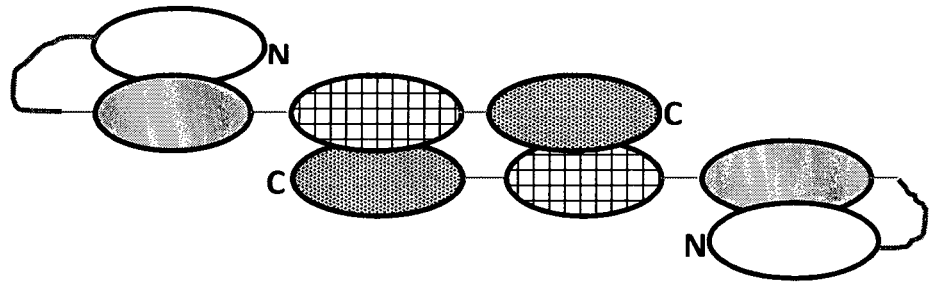
Figure 10:
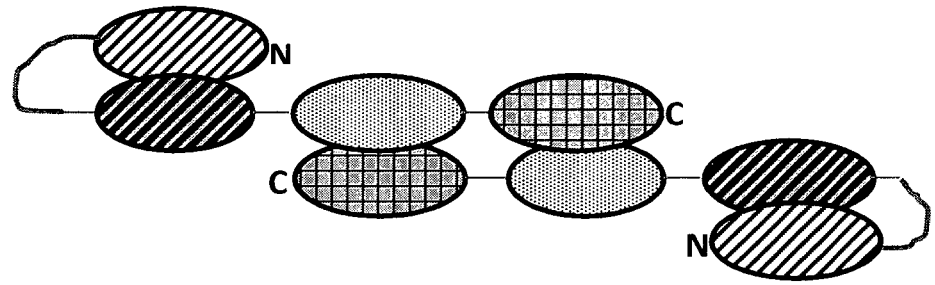
Figure 11A:
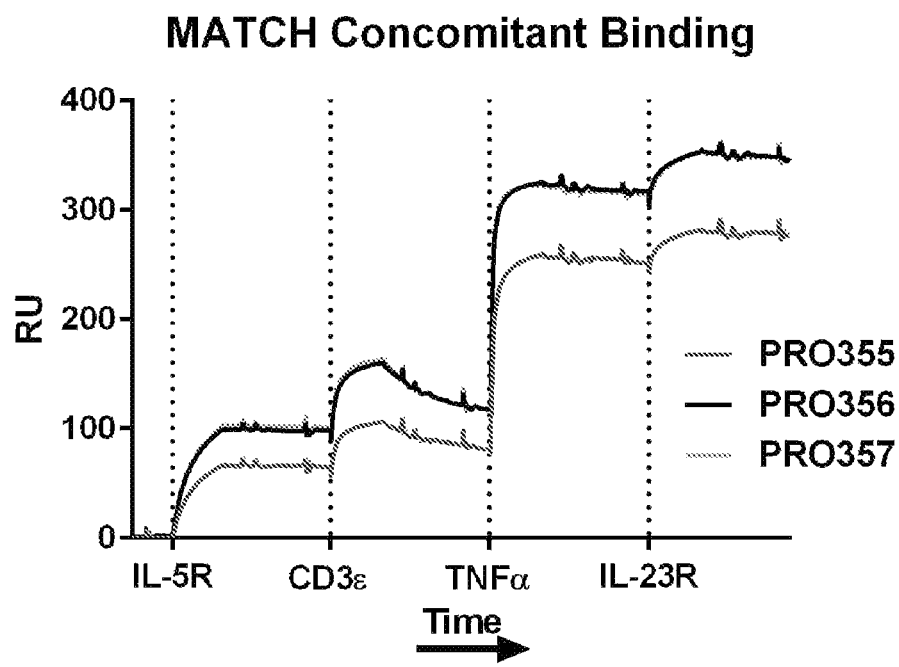
Figure 11B:
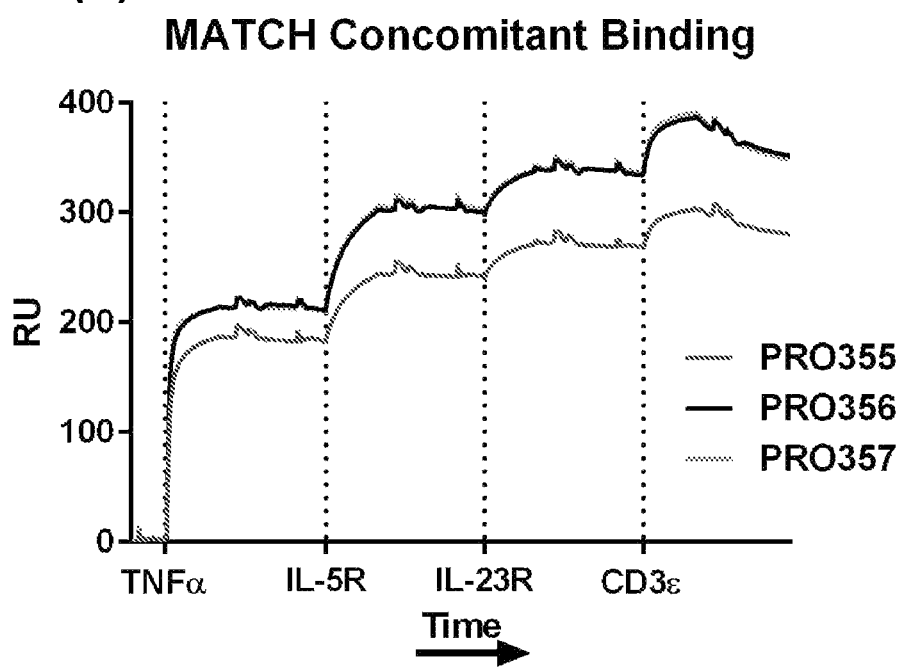
Figure 11C:
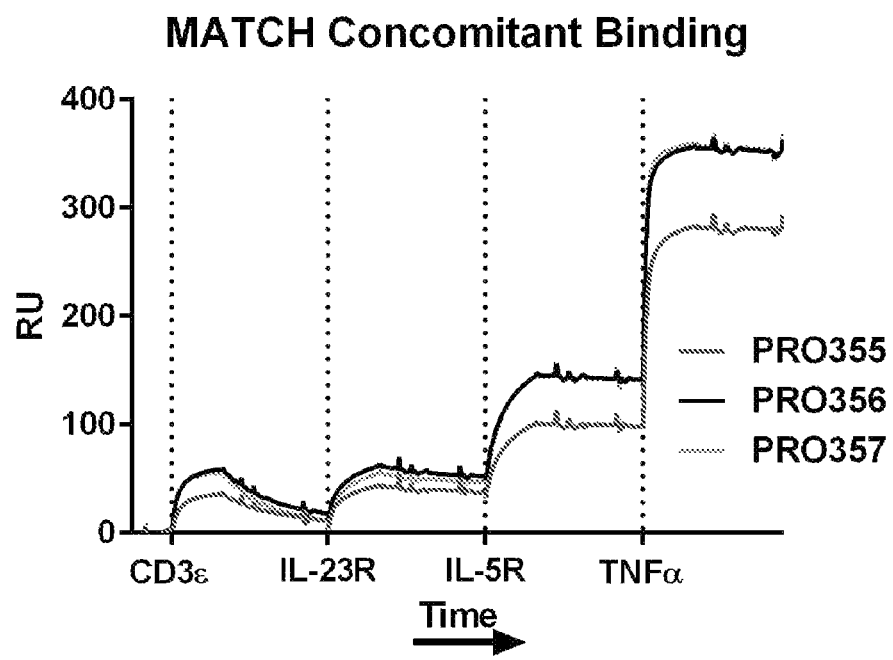
Figure 11D:
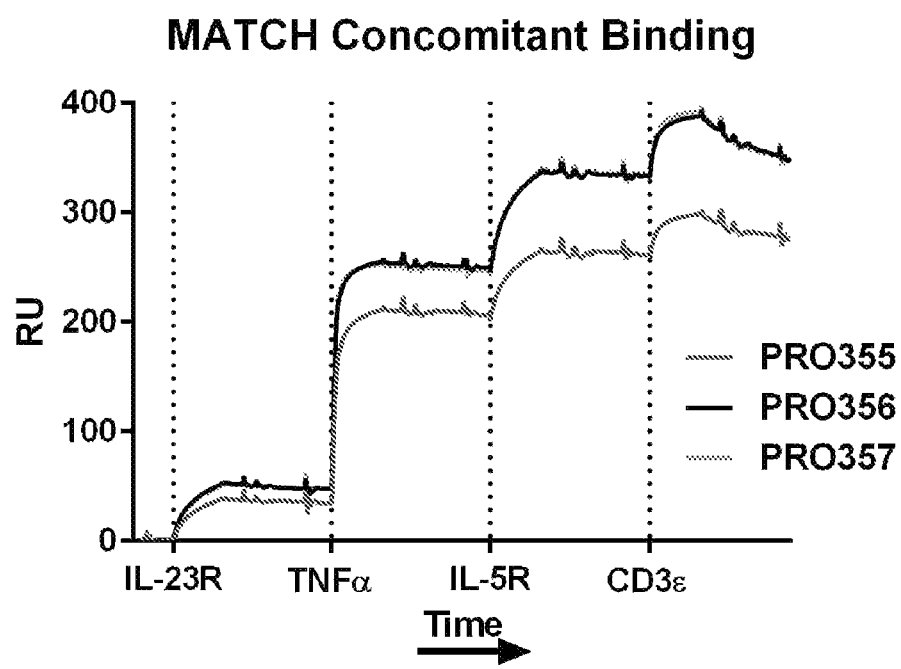
Figure 12A:
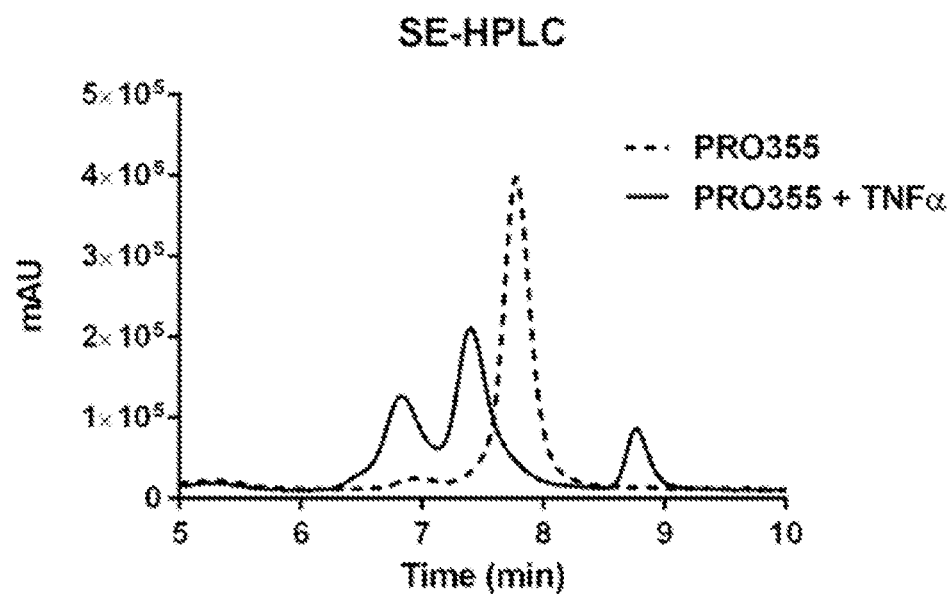
Figure 12B:
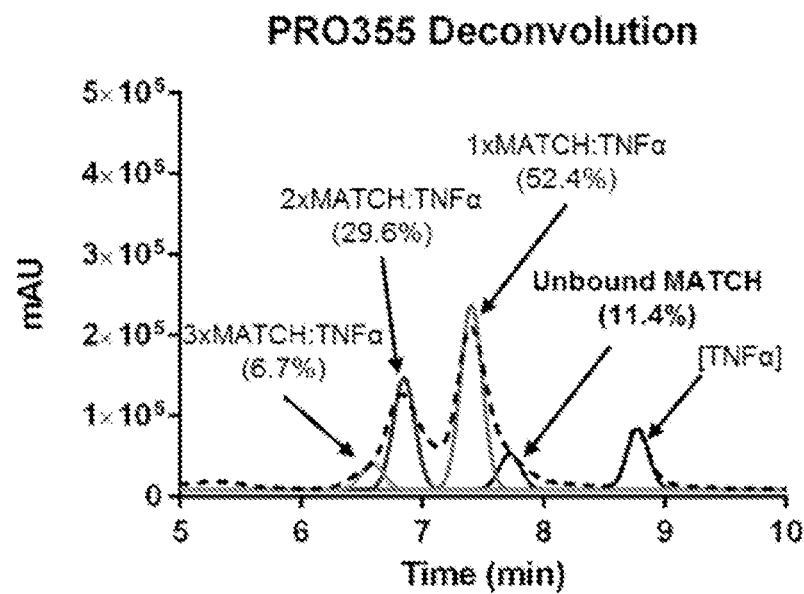
Figure 12C:
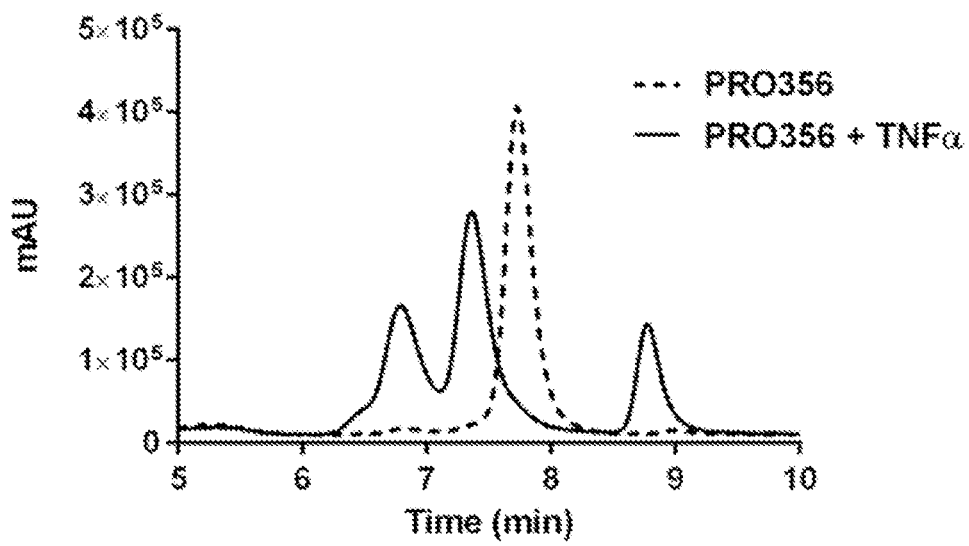
Figure 12D:
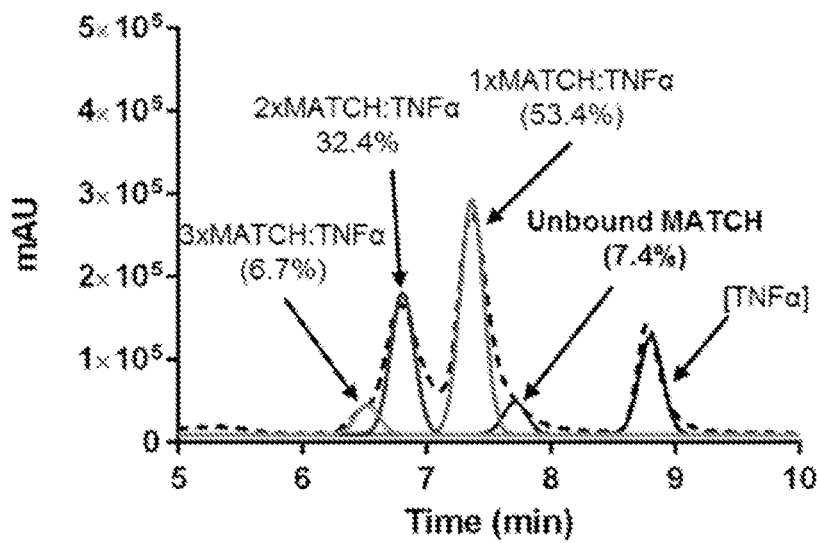
Figure 12E:
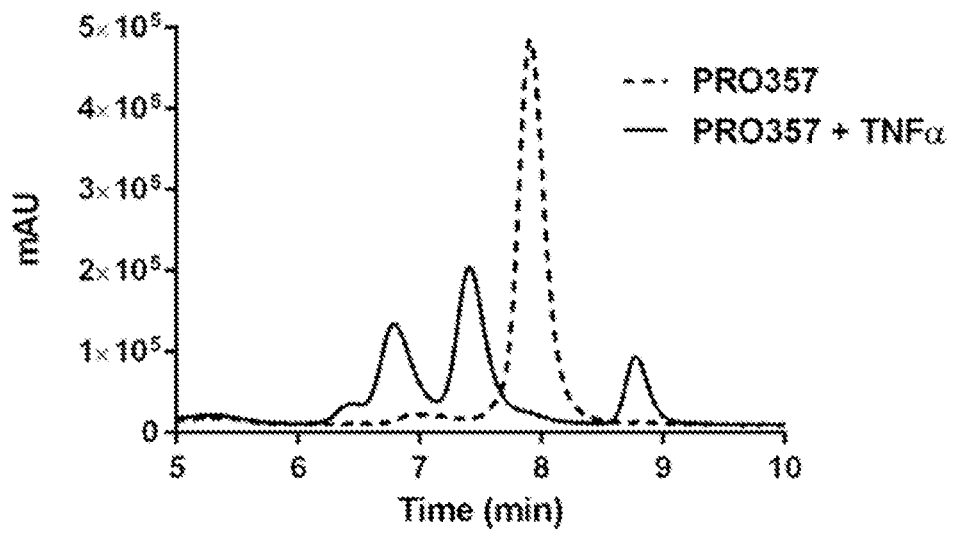
Figure 12F:
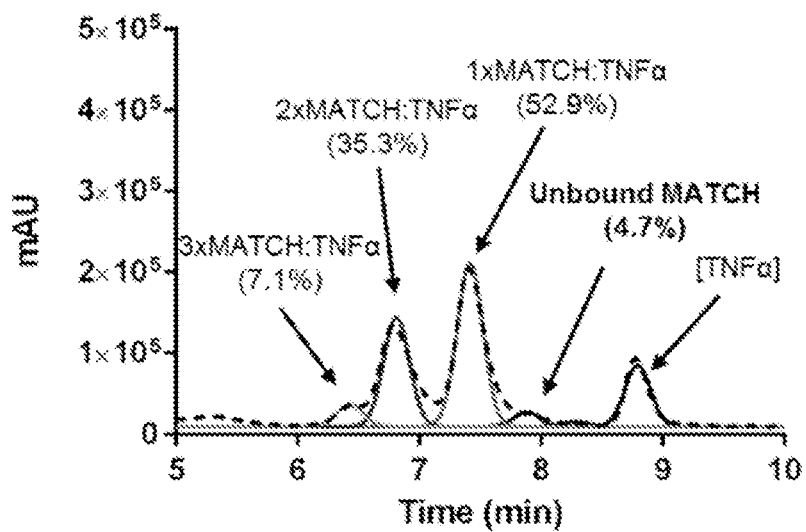

FIG. 10 shows a schematic view of the multi-specific single-chain tandem Fv antibodies according to Kipriyanov et al [R30]: VL: domains: grey background; VH domains: white background; cognate pairs indicated by same filling pattern. (A) Schematic view of single-chains and of hetero-dimeric product. (B) Schematic view of potential homodimers.

FIG. 11 shows the results from an SPR experiment, wherein the MATCH (multispecific antibody-based therapeutics by cognate hetero-dimerization) molecules were immobilized on a sensor chip and the 4 antigens were applied in the indicated sequence. The resulting sensograms (A) to (D) show RU shifts consistent with the simultaneous engagement of all four antigens by each MATCH format.

FIG. 12 shows the results of an analysis of the amount of binding vs. inactive MATCH molecules. The MATCH molecules were pre-incubated with an excess of TNF (antigen for one of the dimer forming Fv domains) and the complex was run over an SE-HPLC. The resulting chromatograms (A) to (F) were analyzed to calculate the fraction of "active" (binding) versus "inactive" MATCH molecule. The analysis revealed between 11.4 to 4.7% inactive protein, when applying a conservative peak fit.

DETAILED DESCRIPTION OF THE INVENTION

Here we present a novel format exhibiting quantitative hetero-dimeric assembly of two protein chains containing multiple antibody variable domains. This format consists of a core of two split variable domain pairs (two Fv fragments) wherein both variable light domains and both variable heavy domains each are positioned on a separate protein chain, thereby driving hetero-dimerization of the two protein chains. Up to two additional variable domains in the scFv format with high intra- and inter-domain stability are fused to the amino- and/or the carboxyl-terminus of either peptide chain, resulting in an up to hexa-specific hetero-dimeric protein.

Thus, in a first aspect the present invention relates to a hetero-dimeric protein comprising a first and a second single-chain protein, wherein said first single-chain protein comprises a first amino acid sequence consisting of (from the N- to the C-terminus):
(ia) a first VL domain;
(iia) a first polypeptide linker and
(iiia) a second VL domain, and
wherein said second single-chain protein comprises a second amino acid sequence consisting of (from the N- to the C-terminus):
(ib) a first VH domain;
(iib) a second polypeptide linker and
(iiib) a second VH domain, and
wherein said first VL domain forms a first cognate pair of variable domains with specificity to a first target antigen with either said first or said second VH domain, and said second VL domain forms a second cognate pair of variable domains with specificity to a second target antigen with the other of said VH domains, and wherein at least one of said first or said second single-chain protein further comprises
(iv) at least one additional domain as third functional domain that is fused via a third polypeptide linker to said first or said second amino acid sequence.

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. With respect to such latter embodiments, the term "comprising" thus includes the narrower term "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

In the context of the present invention, the terms "VL domain" and "VH domain" refer to the variable light chain domain, and the variable heavy chain domain, respectively, of antibodies. In the context of the present invention, the term "antibody" refers to immunoglobulin molecules and immunologically active portions of immunoglobulin molecules, i.e. molecules that contain an antigen binding site that specifically binds to an antigen, i.e. including antibody portions comprising at least an antigen-binding fragment of an antibody.

In the context of the present invention, an antibody, or any binding molecule in general, is considered to "specifically bind" to an antigen (in the case of an antibody), or to a cognate binding partner (in the case of a binding molecule in general), if it has a dissociation constant $K_D$ to said antigen/cognate binding partner as target of 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

In the context of the present invention, the term "functional domains" refers to a proteinaceous domain having a predefined function, such as enzymatic activity or specific binding to a cognate ligand, wherein said proteinaceous domain is a structured domain having at least a secondary structure element. Methods for the determining the presence of secondary structure in polypeptides or proteins, such as X-ray crystallography, circular dichroism (CD), vibrational circular dichroism (VCD), NMR, or FT-IR, or for predicting the presence of secondary structure in polypeptides, such as PEP-FOLD (Shen et al., J. Chem. Theor. Comput. 10 (2014) 4745-4758) are well known to the practitioner in the art. In particular embodiments, said proteinaceous domain is a structured domain having a tertiary structure. In particular embodiments, said proteinaceous domain comprises at least about 20 amino acid residues (see Heitz et al., Biochemistry 38 (1999) 10615-25), particularly at least about 50 amino acid residues, more particularly at least about 100 amino acid residues.

In the context of the present invention, the term "polypeptide linker" refers to a linker consisting of a chain of amino acid residues linked by peptide bonds that is connecting two domains, each being attached to one end of the linker. In particular embodiments, the polypeptide linker has a continuous chain of between 2 and 30 amino acid residues (e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues). In particular embodiments, the polypeptide linker is non-structured polypeptide. As mentioned above, methods for the determining the presence of secondary structure in polypeptides, such as X-ray crystallography, circular dichroism (CD), vibrational circular dichroism (VCD), NMR, or FT-IR, or for predicting the presence of secondary structure in polypeptides, such as PEP-FOLD (Shen et al., J. Chem. Theor. Comput. 10 (2014) 4745-4758) are well known to the practitioner in the art.

This invention is characterized by the following:
- The use of antibody variable domains to create a hetero-dimeric format, where both VL are located on one protein chain while the corresponding VH are located on a second protein chain.
- The hetero-dimeric core domain allows appending of additional functional domains, such as binding domains, to create tri-, tetra-, penta- or hexaspecific entities.
- Multiple examples for highly efficient pairing of the hetero-dimeric core assembly.
- Simple solution to combinatorial screening of multiple binding-domain pools that share a common hetero-dimeric core domain.

In a particular embodiment, the invention relates to a hetero-dimeric protein wherein said first or said second single-chain protein further comprises
(v) a fourth functional domain that is fused via a fourth polypeptide linker to said first or said second amino acid sequence.

In a particular embodiment, the invention relates to a hetero-dimeric protein wherein said first or said second single-chain protein further comprises
(vi) a fifth functional domain that is fused via a fifth polypeptide linker to said first or said second amino acid sequence.

In a particular embodiment, the invention relates to a hetero-dimeric protein wherein said first or said second single-chain protein further comprises
(vii) a sixth functional domain that is fused via a sixth polypeptide linker to said first or said second amino acid sequence.

In particular embodiments, said hetero-dimeric protein comprises said third and said fourth functional domain. In such embodiments, said hetero-dimeric protein is tetravalent, in particular embodiments, said hetero-dimeric protein is tetraspecific.

In particular embodiments, said hetero-dimeric protein comprises said third, said fourth, said fifth and said sixth functional domain. In such embodiments, said hetero-dimeric protein is hexavalent, in particular embodiments, said hetero-dimeric protein is hexaspecific.

In particular embodiments, said hetero-dimeric protein does not comprise a cognate pair of a first and a second immunoglobulin constant domain, wherein said first immunoglobulin constant domain is comprised in said first single-chain protein and wherein said second immunoglobulin constant domain is comprised in said second single-chain protein. In particular embodiments, at least one of said first and said second single-chain proteins does not comprise an immunoglobulin constant domain. In a particular embodiment, both said first and said second single-chain proteins do not comprise an immunoglobulin constant domain.

In particular embodiments, said hetero-dimeric protein does not comprise a cognate pair of a first proteinaceous interaction domain comprised in said first single-chain protein and a second proteinaceous interaction domain comprised in said second single-chain protein other than the cognate pairs of (i) said first VL domain and said first VH domain and (ii) said second VL domain and said second VH domain.

In particular embodiments, said first polypeptide linker consists of from 5 to 20 amino acid residues, particularly from 6 to 15 amino acid residues. In particular embodiments, said polypeptide linker has the sequence $(G_mS)_n$; with m being independently selected from 2, 3, and 4; and n being selected from 1, 2, 3, 4, and 5.

In particular other embodiments, said first polypeptide linker consists of from 11 to 20 amino acid residues, particularly from 11 to 15 amino acid residues. In particular embodiments, said polypeptide linker has the sequence $(G_mS)_n$; with m being independently selected from 2, 3, and 4; and n being selected from 3, 4, and 5.

In particular embodiments, said second polypeptide linker consists of from 5 to 20 amino acid residues, particularly from 6 to 15 amino acid residues. In particular embodiments, said polypeptide linker has the sequence $(G_mS)_n$; with m being independently selected from 2, 3, and 4; and n being selected from 1, 2, 3, 4, and 5.

In particular other embodiments, said second polypeptide linker consists of from 11 to 20 amino acid residues, particularly from 11 to 15 amino acid residues. In particular embodiments, said polypeptide linker has the sequence $(G_mS)_n$; with m being independently selected from 2, 3, and 4; and n being selected from 3, 4, and 5.

In particular embodiments, said third, fourth, fifth and/or sixth polypeptide linkers independently consist of from 8 to 20 amino acid residues, particularly from 10 to 15 amino acid residues. In particular embodiments, said polypeptide linkers independently have the sequence $(G_mS)_n$; with m being independently selected from 2, 3, and 4, particularly 4; and n being selected from 1, 2, 3, 4, and 5, particularly from 2 and 3.

In particular embodiments, said first VL domain (ia) and said first VH domain (ib) form a first cognate pair of variable domains with specificity to a first target antigen, and said second VL domain (iia) and said second VH domain (iib) form a second cognate pair of variable domains with specificity to a second target antigen. In such embodiment, said first and said second single-chain protein form said hetero-dimeric protein in a parallel arrangement of said single-chain proteins.

In particular such embodiments, said first polypeptide linker consists of from 10 to 20 amino acid residues, particularly from 12 to 17 amino acid residues, particularly 15 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 3.

In particular such embodiments, said second polypeptide linker consists of from 10 to 20 amino acid residues, particularly from 12 to 17 amino acid residues, particularly 15 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 3.

In particular such embodiments, said third, fourth, fifth and/or sixth polypeptide linkers independently consist of from 10 to 20 amino acid residues, particularly from 12 to 17 amino acid residues, particularly 15 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 3.

In particular other embodiments, said first VL domain (ia) and said second VH domain (iib) form a first cognate pair of variable domains with specificity to a first target antigen, and said second VL domain (iia) and said first VH domain (ib) form a second cognate pair of variable domains with specificity to a second target antigen. In such embodiment, said first and said second single-chain protein form said hetero-dimeric protein in an anti-parallel arrangement of said single-chain proteins.

In particular such embodiments, said first polypeptide linker consists of from 5 to 12 amino acid residues, particularly from 5 to 10 amino acid residues, particularly 6 amino acid residues. In particular embodiments, said polypeptide linker has the sequence $(G_mS)_n$; with m being independently selected from 2, 3, and 4, particularly 2; and n being selected from 1, 2, 3, 4, and 5, particularly 2.

In particular such embodiments, said second polypeptide linker consists of from 5 to 12 amino acid residues, particularly from 6 to 10 amino acid residues, particularly 8 amino acid residues. In particular embodiments, said polypeptide linker has the sequence $(G_mS)_n$; with m being independently selected from 2, 3, and 4, particularly 3; and n being selected from 1, 2, 3, 4, and 5, particularly 2.

In particular such embodiments, said third, fourth, fifth and/or sixth polypeptide linkers independently consist of from 10 to 20 amino acid residues, particularly from 8 to 12 amino acid residues, particularly 10 amino acid residues. In particular embodiments, said polypeptide linker has the sequence $(G_mS)_n$; with m being independently selected from 2, 3, and 4, particularly 4; and n being selected from 1, 2, 3, 4, and 5, particularly 2.

In particular embodiments, said third, fourth, fifth and/or sixth functional domains are independently selected from the list of: binding domains, toxins, enzymes, hormones, signaling proteins, and albumins.

In particular embodiments, said third, fourth, fifth and/or sixth functional domains are independently selected from binding domains.

In particular such embodiments, binding domains are independently selected from the list of: antibody-based binding domains including but not limited to scFv, Fab and single antibody variable domains, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology)

In particular such embodiments, said binding domains are antibody-based binding domains selected from: single-chain Fv fragments and single antibody variable domains.

Figure 1:
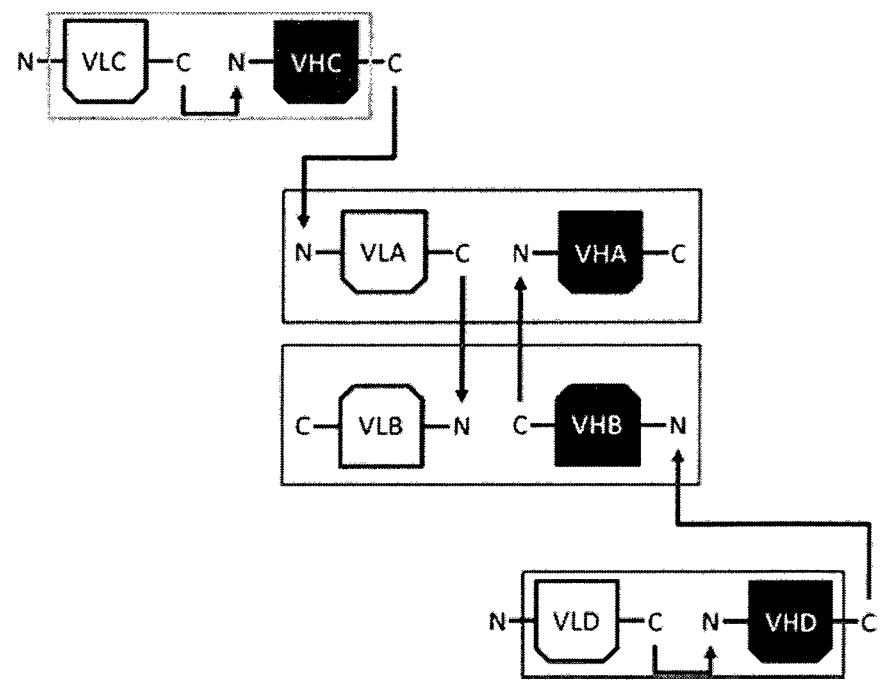
FIG. 1 shows a schematic representation of Assembly 1 (see Example 1).
Figure 4:
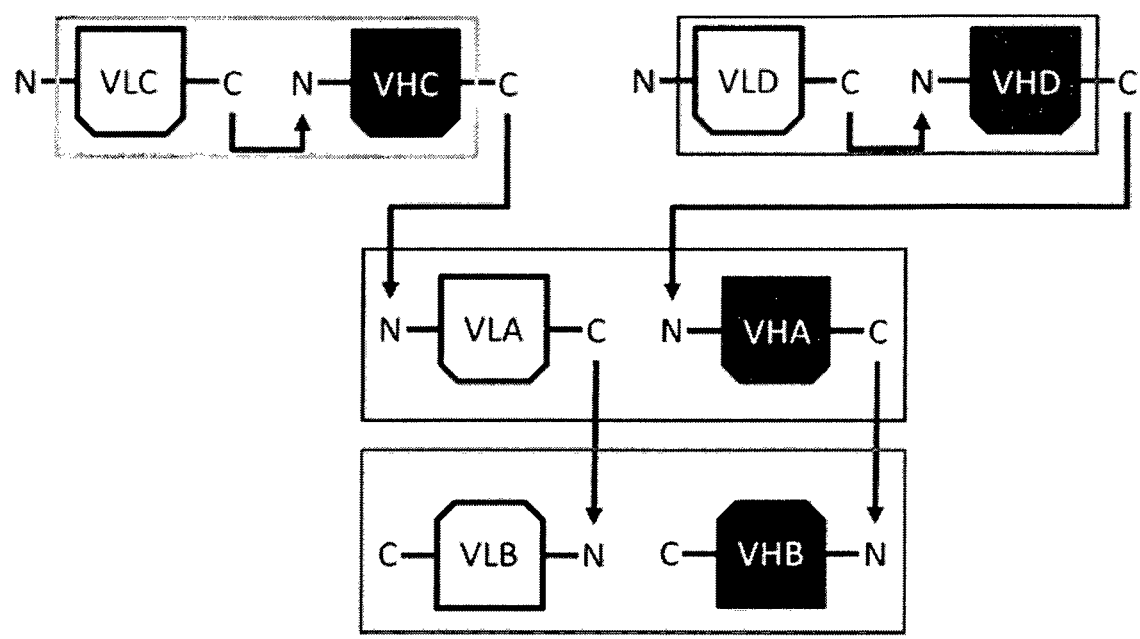
FIG. 4 shows a schematic representation of Assembly 7 (see Example 1).
Figure 5A:
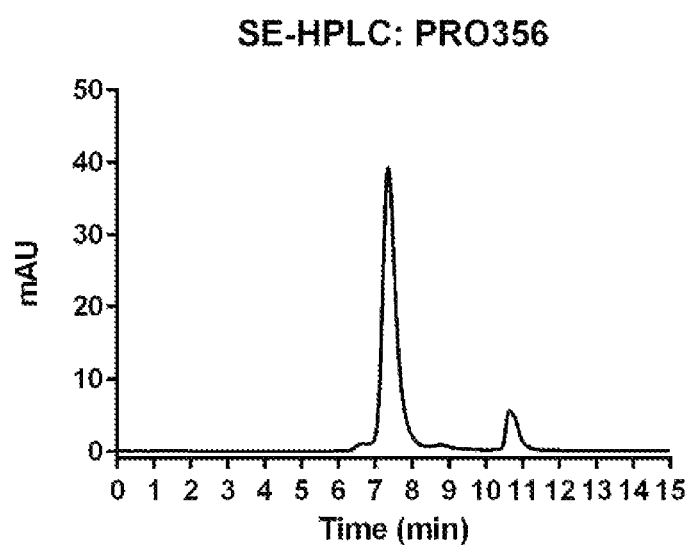
FIG. 5 shows the size exclusion chromatograms after 1-step purification. (A) Assembly 1; (B) Assembly 3; (C) Assembly 5; (D) Assembly 7.
Figure 5B:
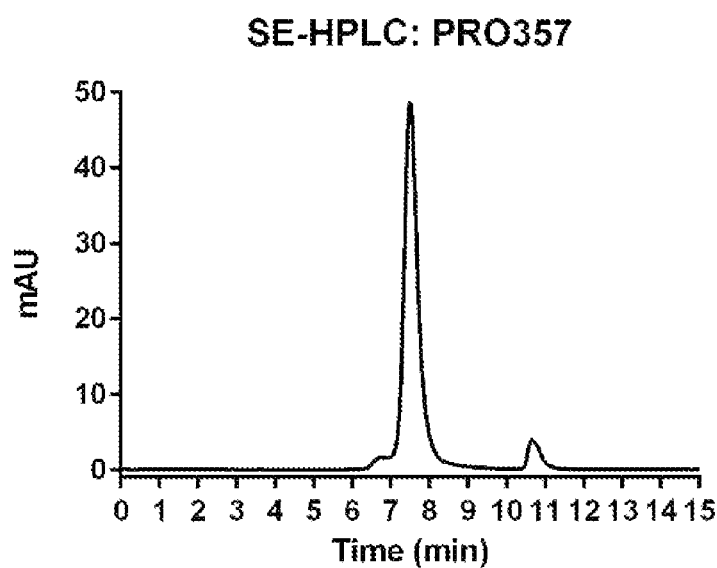
Figure 5C:
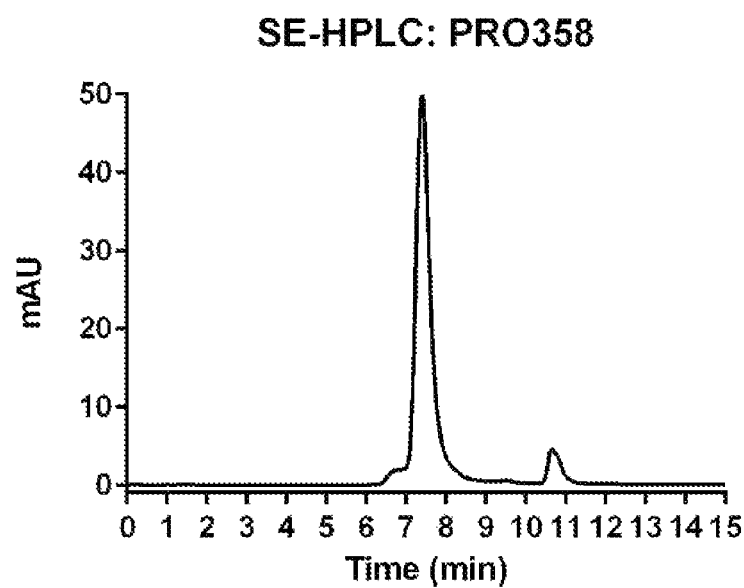
Figure 5D:
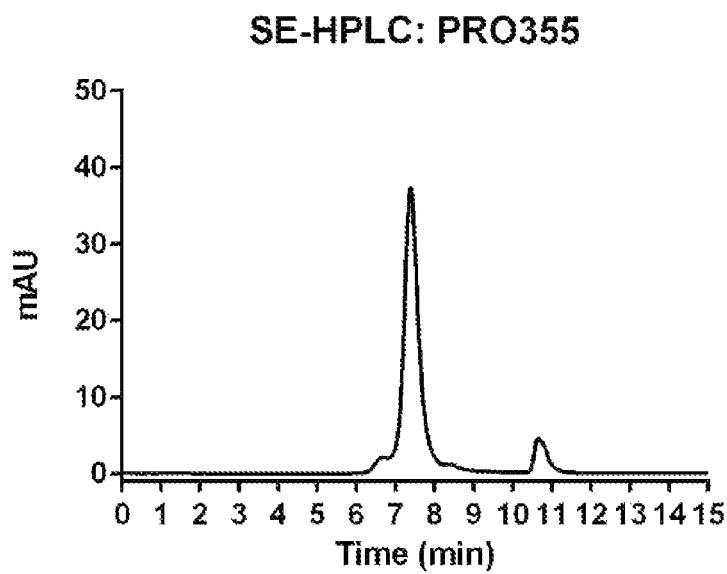

In certain such embodiments, the order of variable domain in such a single chain Fv fragment is selected from (from N-terminus to C-terminus) VL-(linker)-VH and VH-(linker)-VL. In certain embodiments, the order of variable domains is the same for all single-chain Fv fragments comprised in the hetero-dimeric protein. In certain embodiments, three VL domains are linked to each other by said first polypeptide linker and one of said third, fourth and fifth polypeptide linkers, respectively, for example where a single-chain Fv fragment in the order VL-(linker)-VH is C-terminal from said first amino acid sequence. In certain embodiments, three VH domains are linked to each other by said second polypeptide linker and one of said third, fourth and fifth polypeptide linkers, respectively, for example where a single-chain Fv fragment in the order VL-(linker)-VH is N-terminal from said second amino acid sequence (see FIGS. 1 and 4). Thus, in certain embodiments at least one of said first and said second single-chain proteins comprises an amino acid sequence consisting of three VL domains or three VH domains, respectively, linked by two polypeptide linkers.

Figure 3:
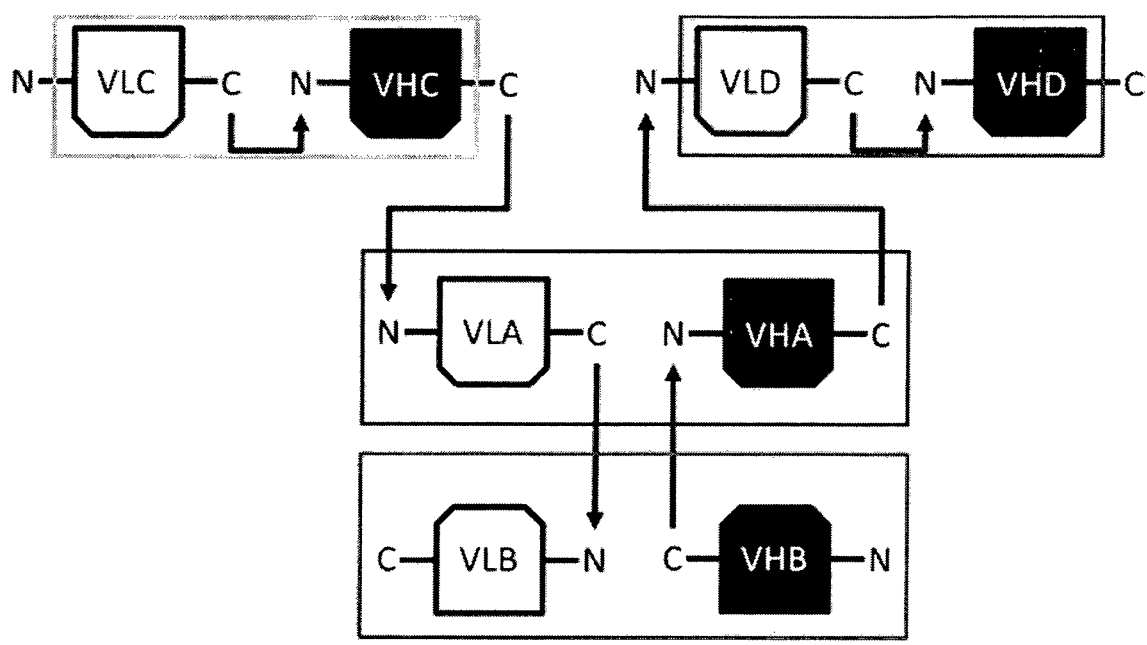
FIG. 3 shows a schematic representation of Assembly 5 (see Example 1).

In certain other embodiments, the variable domain of any such antibody-based binding domain that is directly linked via the corresponding linker to the N- and/or the C-terminus of said first or second amino acid sequence is (a) a VH domain in case that it is fused to said first amino acid sequence, and (b) a VL domain in case that it is fused to said second amino acid sequence. Thus, a VH domain is fused to the N- and/or the C-terminus of a VL-linker-VL core region, and a VL domain is fused to the N- and/or the C-terminus of a VH-linker-VH core region (see, for example, FIG. 3).

In particular embodiments, said third, fourth, fifth and/or sixth binding domains are single-chain Fv fragments.

In particular such embodiments, the polypeptide linker connecting the variable domains of said single-chain Fv fragments consists of between 15 and 25 amino acid residues, particularly 20 amino acid residues. In particular embodiments, said polypeptide linker has the sequence $(GGGGS)_n$, with n being selected from 3, 4, and 5, particularly 4.

In particular embodiments, the at least one of said antibody variable domains comprises CDR regions derived from a parental rabbit antibody.

In particular embodiments, at least one of said antibody variable domains comprises human framework regions.

In particular such embodiments, at least one of said VL domains comprises (i) human Vκ framework regions I to III; (ii) CDR domains CDR1, CDR2 and CDR3; and (iii) a framework region IV, which is selected from a. a human Vλ germ line sequence for framework region IV, particularly a Vλ germ line sequence selected from the list of: SEQ ID NO. 16 to 22 according to WO 2014/206561;

b. a Vλ-based sequence, which is (bi) a consensus Vλ sequence from human Vλ germ line sequences for framework region IV, particularly SEQ ID NO. 17 according to WO 2014/206561; or (bii) a consensus Vλ sequence from rearranged human Vλ sequences for framework region IV, particularly a Vλ consensus sequence selected from the list of: SEQ ID NO. 16 and 17 according to WO 2014/206561; and c. a Vλ-based sequence, which has one or two mutations, particularly one mutation, compared to the closest human Vλ germ line sequence for framework region IV.

In certain embodiments, the cognate pair of one of said first and said second VL and VH domains is specific for an antigen selected from the list of: a cancer target; and a target present on immune effector cells, such as CD3.

In particular such embodiments, said third, fourth, fifth and/or sixth binding domains are single-chain Fv fragments with specificity for a target selected from the list of: a cancer target, and a target present on immune effector cells, such as CD3.

In the context of the present application the term "target" refers to a cognate binding partner of a binding domain, such as an antigen of an antibody that is specifically bound by such binding domain.

In particular embodiments, said target is a cancer target, in particular an antigen or an epitope that is present on the surface of one or more tumour cell types or tumour-associated cells in an increased concentration and/or in a different steric configuration as compared to the surface of non-tumour cells. Particularly, said cancer target is present on the surface of one or more tumour or tumour stroma cell types, but not on the surface of non-tumour cells.

In other particular embodiments, said target is an antigen or epitope that is preferentially expressed on cells involved in autoimmune diseases. In other embodiments, said antigen or epitope is preferentially expressed on cells involved in an inflammatory disease.

In particular embodiments, said target is a target present on immune effector cells. In particular embodiments, said target is CD3.

In certain embodiments, said first and said second single-chain protein are selected from the following list, wherein VLA, VLB, VHA, and VHB correspond to said first and second VL and VH domains, and VLC, VLD, VLE, VLF, VHC, VHD, VHE, and VHF are part of single-chain fragments with a linker corresponding to said third, fourth, fifth and/or sixth functional domain, respectively, linked via third, fourth, fifth and/or sixth linkers LINKER3, LINKER4, LINKER5 and LINKER6) to the core domain (in bold letters); all constructs are written in the direction N- to C-terminus:

A (parallel; 6Fvs):

```
chain 1:
VLC-(linker)-VHC-(LINKER3)-VLA-(LINKER1)-VLB-
(LINKER4)-VLD-(linker)-VHD chain 2:
VLE-(linker)-VHE-(LINKER5)-VHA-(LINKER2)-VHB-
(LINKER6)-VLF-(linker)-VHF
```

B (anti-parallel 6Fvs):

```
chain 1:
VLC-(linker)-VHC-(LINKER3)-VLA-(LINKER1)-VLB-
(LINKER4)-VLD-(linker)-VHD chain 2:
VLE-(linker)-VHE-(LINKER52)-VHB-(LINKER2)-VHA-
(LINKER6)-VLF-(linker)-VHF
```

C1 (anti-parallel 4 Fvs) (see FIG. 1):

```
chain 1:
VLC-(linker)-VHC-(LINKER3)-VLA-(LINKER1)-VLB chain 2:
VLD-(linker)-VHD-(LINKER4)-VHB-(LINKER2)-VHA
```

C2 (anti-parallel 4 Fvs) (see FIG. 3):

```
chain 1:
VLC-(linker)-VHC-(LINKER3)-VLA-(LINKER1)-VLB chain 2:
VHB-(LINKER2)-VHA-(LINKER4)-VLD-(linker)-VHD
```

C3 (anti-parallel 4 Fvs):

```
chain 1:
VLA-(LINKER1)-VLB-(LINKER3)-VLC-(linker)-VHC chain 2:
VLD-(linker)-VHD-(LINKER4)-VHB-(LINKER2)-VHA
```

C4 (anti-parallel 4 Fvs):

```
chain 1:
VLA-(LINKER1)-VLB-(LINKER3)-VLC-(linker)-VHC chain 2:
VHB-(LINKER2)-VHA-(LINKER4)-VLD-(linker)-VHD
```

D1 (parallel 4 Fvs) (see FIG. 4):

```
chain 1:
VLC-(linker)-VHC-(LINKER3)-VLA-(LINKER1)-VLB chain 2:
VLD-(linker)-VHD-(LINKER4)-VHA-(LINKER2)-VHB
```

D2 (parallel 4 Fvs):

```
chain 1:
VLC-(linker)-VHC-(LINKER3)-VLA-(LINKER1)-VLB
```

```
chain 2:
VHA-(LINKER2)-VHB-(LINKER4)-VLD-(linker)-VHD
```

D3 (parallel 4 Fvs):

```
chain 1:
VLA-(LINKER1)-VLB-(LINKER3)-VLC-(linker)-VHC chain 2:
VLD-(linker)-VHD-(LINKER4)-VHA-(LINKER2)-VHB
```

D4 (parallel 4 Fvs):

```
chain 1:
VLA-(LINKER1)-VLB-(LINKER3)-VLC-(linker)-VHC chain 2:
VHA-(LINKER2)-VHB-(LINKER4)-VLD-(linker)-VHD
```

In this format the localization of two split variable heavy domains VHB and VHC on one protein chain and the two corresponding variable light domains VLB and VLC on the other protein chain (VH-VH/VL-VL) prevents the formation of intra-chain domain pairings resulting in inactive single-chain diabody (scDb)-like structures as it would be the case if the VH-VL/VH-VL orientation of the conventional diabody—similar to the design suggested by Kipriyanov et al—had been used to drive hetero-dimerization. In contrast, the VH-VH/VL-VL-orientation forces the formation of exclusively hetero-dimeric bi- to hexa-specific proteins.

There is the theoretical possibility that the VH/VL domain pairing of the target A and B binding VHA-VHB/VLA-VLB core domain would result in an inactive core domain due to the inappropriate pairing of VHA with VLB and VHB with VLA resulting in VHA-VLB and VHB-VLA pairs. Unexpectedly and surprisingly, such inactive variants have not been observed so far. Without wishing to be bound by theory, dimerization could be driven towards cognate pairing due to the more efficient packing of the CDRs of cognate pairs as opposed to potential packing interferences occurring in non-matching pairings.

In order to further drive the hetero-dimerization towards active pairing in the VH-VH/VL-VL core domain, the knob-into-hole or similar technologies could be applied in one or—if reciprocally applied—both VL/VH pairs of the VH-VH/VL-VL core domain. Thus, in certain embodiments, the active pairing in the VH-VH/VL-VL core domain of said hetero-dimeric protein is further supported by a technology selected from: knob-into-hole, and inter-chain cysteine bridges.

In a second aspect, the present invention relates to one or two nucleic acid sequences encoding said first and a second single-chain proteins.

In a third aspect, the present invention relates to one or two vectors comprising said one or two nucleic acid sequences.

In a fourth aspect, the present invention relates to a host cell or host cells comprising one or two vectors.

In a fourth aspect, the present invention relates to a method for producing the first and second single-chain proteins, or the hetero-dimeric protein, of the present invention, comprising (i) providing a nucleic acid or nucleic acids according to the present invention, or a vector or vectors according to the present invention, expressing said nucleic acid or nucleic acids or said vector or vectors and collecting said first and second single-chain proteins, or said hetero-dimeric protein, from the expression system, or (ii) providing a host cell or host cells of the present invention, culturing said host cell or host cells, and collecting said first and second single-chain proteins, or said hetero-dimeric protein, from the cell culture.

In a fifth aspect, the present invention relates to a pharmaceutical composition comprising the hetero-dimeric protein of the present invention and a pharmaceutically acceptable carrier.

In a sixth aspect, the present invention relates to the hetero-dimeric protein of the present invention for use in the treatment of a disease selected from cancer, an inflammatory and an autoimmune disease, wherein at least one of said cognate pairs of VL and VH domains, or of said third, fourth, fifth, or sixth functional domain is able to specifically interact with a target of therapeutic relevance in the corresponding disease.

In a seventh aspect the present invention relates to a method for treating a patient suffering from a disease selected from cancer, an inflammatory and an autoimmune disease, comprising administering to a subject an effective amount of the hetero-dimeric protein of the present invention, wherein at least one of said cognate pairs of VL and VH domains, or of said third, fourth, fifth, or sixth functional domain is able to specifically interact with a target of therapeutic relevance in the corresponding disease.

LITERATURE

R1. Skerra, A., and Plückthun, A. (1988). Assembly of a functional immunoglobulin Fv fragment in *Escherichia coli*. Science 240, 1038-1041.

R2. Röthlisberger et al., (2005). Domain interactions in the Fab fragment: A comparative evaluation of the single-chain Fv and Fab format engineered with variable domains of different stability. J Mol Biol 347, 773-789.

R3. Ridgway et al., 1996. 'Knobs-into-holes' engineering of antibody CH3 domains for heavy chain heterodimerization. Protein Eng. 9, 617-621.

R4. Zhu (1997) Remodeling domain interfaces to enhance heterodimer formation. Protein Sci. 6, 781-788

R5. Schaefer, W., et al., 2011b. Immunoglobulin domain crossover as a generic approach for the production of bispecific IgG antibodies. Proc. Natl. Acad. Sci. U.S.A. 108, 11187-11192.

R6. Holliger et al., "Diabodies": small bivalent and bispecific antibody fragments. Proc. Natl. Acad. Sci. U.S.A. 90, 6444-6448.

R7. Arndt et al., 1999. A bispecific diabody that mediates natural killer cell cytotoxicity against xeno-transplantated human Hodgkin's tumors. Blood 94, 2562-2568.

R8. Kipriyanov et al., 1999. Bispecific tandem diabody for tumor therapy with improved antigen binding and pharmacokinetics. J. Mol. Biol. 293, 41-56.

R9. Alt et al., 1999. Novel tetravalent and bispecific IgG-like antibody molecules combining single-chain diabodies with the immunoglobulin gamma1 Fc or CH3 region. FEBS Lett. 454, 90-94.

R10. Johnson et al., 2010. Effector cell recruitment with novel Fv-based dual-affinity retargeting protein leads to potent tumor cytolysis and in vivo B-cell depletion. J. Mol. Biol. 399, 436-449.

R11. De Jonge et al., (1995) Production and characterization of bispecific single-chain antibody fragments. Mol. Immunol. 32, 1405-1412.

R12. Reiter et al., (1994) Engineering interchain disulfide bonds into conserved framework regions of Fv fragments:

improved biochemical characteristics of recombinant immunotoxins containing disulfide-stabilized Fv. Protein Eng. 7, 697-704.

R13. Pack, P., and Plückthun, A. (1992). Miniantibodies: Use of amphipathic helices to produce functional, flexibly linked dimeric Fv fragments with high avidity in *Escherichia coli*. Biochemistry 31, 1579-1584.

R14. Schoonjans et al., Fab chains as an efficient heterodimerization scaffold for the production of recombinant bispecific and trispecific antibody derivatives. J Immunol. 2000 Dec. 15; 165(12):7050-7.

R15. Orcutt et al., 2009. A modular IgG-scFv bispecific antibody topology. Pro-tein Eng. Des. Sel. 23, 221-228.

R16. Wu, C. et al., 2007. Simultaneous targeting of multiple disease mediators by a dual-variable-domain immunoglobulin. Nat. Biotechnol. 25, 1290-1297.

R17. "mAbs"; Köhler & Milstein, Nature. 256 (1975) 495-7

R18. Umaña et al., 1999. Engineered glycoforms of an antineuroblastoma IgG1 with optimized antibody-dependent cellular cytotoxic activity. Nat. Biotechnol. 17, 176-180

R19. Yu, Y. J. et al. Sci. Trans. Med. 3, 84ra44 (2011).

R20. Hinton P R. et al., 2004. Engineered human IgG antibodies with longer serum half-lives in primates. J Biol Chem. 279(8):6213-6.

R21. Spiess et al., 2015. Alternative molecular formats and therapeutic applications for bispecific antibodies. Mol Immunol. 2015 Jan. 27.

R22. Davis et al., 2013. Readily isolated bispecific antibodies with native immunoglobulin format. U.S. Pat. No. 8,586,713. Regeneron Pharmaceuticals, Inc.

R23. Shahied L S, et al., Bispecific minibodies targeting HER2/neu and CD16 exhibit improved tumor lysis when placed in a divalent tumor antigen binding format. J Biol Chem. 2004 Dec. 24; 279(52):53907-14. Epub 2004 Oct. 7.

R24. Milstein. C and Cuello. A. C. (1983) Nature, 305, 537-54

R25. Chang et al., The dock and lock method: a novel platform technology for building multivalent, multifunctional structures of defined composition with retained bioactivity. Clin Cancer Res. 2007 Sep. 15; 13(18 Pt 2):5586s-5591s.

R26. Deyev et al., (2003). Design of multivalent complexes using the barnase•barstar module. Nature biotechnology, 21(12), 1486-1492.

R27. Pack, P., and Plückthun, A. (1992). Miniantibodies: Use of amphipathic helices to produce functional, flexibly linked dimeric Fv fragments with high avidity in *Escherichia coli*. Biochemistry 31, 1579-1584.

R28. Halin et al. (2003). Synergistic therapeutic effects of a tumor targeting antibody fragment, fused to interleukin 12 and to tumor necrosis factor α. Cancer research, 63(12), 3202-3210.

R29. D. Müller et al., Improved pharmacokinetics of recombinant bispecific antibody molecules by fusion to human serum albumin J. Biol. Chem., 282 (2007), pp. 12650-12660

R30. EP1293514

R31. Milstein C, and Cuello A C (1983) Hybrid hybridomas and their use in immunohistochemistry. Nature 305:537-540

EXAMPLES

Example 1: Construction of Multispecific Formats

For the construction of the hetero-dimeric multi-specific formats that were named multispecific antibody-based therapeutics by cognate hetero-dimerization (MATCH), four well characterized variable domains were chosen that are directed against human tumor necrosis factor alpha (TNF), human interleukin-5 receptor (IL5R), human CD3 epsilon (CD3) and interleukin-23 receptor (IL23R), respectively. Based on the known binding characteristics of the respective variable domains in the scFv format, the activity and thereby correct association of cognate VL/VH pairs was assessed in the context of the multi-specific molecules. The respective variable domains in the periphery of the molecule were either located at the amino (N)-terminus or the carboxyl (C)-terminus of each protein chain as single-chain Fv (scFv) fragments, or located in the hetero-dimerization core domain. In contrast to the peripheral scFv fragments for which the VL and VH were positioned on the same protein chain, the cognate variable domains VL and VH of the core domain were located on the two different protein chains. In the examples presented below the target-binding domains located in the two core domains are directed against CD3 or TNF, respectively. The variable domains binding to IL23R or IL5R have been used for the peripheral scFv modules that were fused either to the N- or C-terminus of the core domain using a flexible amino acid linker of 10 or 15 amino acids.

In order to explore different variations of the hetero-dimeric core assembly presented herein, the parallel as well as the anti-parallel orientation of the cognate variable domain pairs have been generated, each with either one or two additional scFv modules appended to the N or C-terminus of the core domain.

In the antiparallel arrangement, the core domain has been constructed in the orientation VHA-VHB/VLB-VLA, from N-terminus to C-terminus of each protein chain (protein chains 1 through 9). In one embodiment a tetra-specific format is formed by an N-terminal fusion of one scFv module to each of the two protein chains (constructs consisting of protein chains 1+2). The corresponding tri-specific format contains a scFv module fused to only one of the two protein chains (Constructs 1+5). To investigate possible stabilization effects of the core domain assembly by engineered disulfide bridges, the two formats above have been generated also with a C-terminal cysteine that results in a crosslink of the cognate Fvs in the core domain of each protein chain. The respective hetero-dimeric formats consist of protein chains 3+4, for the tetra-specific format and protein chains 4+6 for the tri-specific format. In a variation of the antiparallel arrangement the scFv module located on the chain containing the tandem VH in the core domain was fused to the C-terminus instead of the N-terminus and was combined with a protein chain containing the assembled scFv module at the N-terminus resulting in a tetra-specific format (protein chains 1+7) or with protein chain containing only a core domain resulting in a tri-specific format (protein chains 5+7).

In the parallel arrangement, the core domain has been constructed in the orientation VHA-VHB/VLA-VLB, from N-terminus to C-terminus of each protein chain arrangement. A tetra-specific format, with both scFv modules fused to the N-terminal side of the core domains, was generated by co-expression of the protein chains 9+10. The corresponding trispecific assembly, with a scFv module solely on the tandem VH containing chain, was generated by co-expression of protein chains 10+11.

To generate the constructs outlined in Table 1 the amino acid sequences for the Fv domains and linkers were back-translated into corresponding nucleic sequences, which were de novo synthesized. The coding sequences were assembled and cloned by standard molecular biology techniques (e.g.

Sambrook, J., et al., Molecular Cloning: A Laboratory Manual) into a suitable expression vector (e.g. pcDNA3.1, Invitrogen) for recombinant protein secretion.

Example 2: Expression and Purification

The expression of the multispecific format assemblies was performed by co-transfection of the constructs into a suspension cell line (e.g. CHO-S Freestyle™, Invitrogen) by using a transient gene expression protocol (FreeStyle™ MAX system). The combination of the co-expressed expression vectors for the generation of the multispecific format assemblies is outlined in Table 2. After cultivation for several days the supernatant of the antibody fragment secreting cells was recovered for purification. The protein was captured on a suitable affinity resin (e.g. Capto L, GE Healthcare), washed extensively and eluted by a pH shift. The eluted protein was neutralized and buffer exchanged to yield the purified pools. The proteins were analyzed by size-exclusion high-performance liquid chromatography (SE-HPLC) (Table 3 and FIG. 5) and sodium dodecyl sulfate polyacrylamide gel electrophoresis (SDS-PAGE) (FIG. 6) for purity and UV/Vis spectroscopy for protein content. The protein concentration was adjusted to the required levels and the stability analysis was performed.

Using a single step affinity chromatography procedure all constructs could be eluted in a highly pure and monomeric fraction (FIGS. 5 and 6), confirming the efficient and correct pairing of cognate variable domains. Furthermore, in a non-reducing SDS-Page PRO357 migrated almost quantitatively at a size of a covalently linked hetero-dimer (~106 kDa), supporting appropriate inter-MATCH chain associations and demonstrating the highly efficient and near complete formation of the inter chain disulfide bond. Due to structural constraints the formation of this disulfide bond between miss paired variable domains is very unlikely. Therefore, this result suggests that hetero-dimerization occurred almost exclusively between cognate variable domain pairs.

Example 3: Storage Stability Assessment

Efficient MATCH chain dimerization was further demonstrated by the remarkable homogeneity of the protein content in protein L-purified samples. The protein was analyzed over the course of four weeks and storage at 4° C. and 37° C. with respect to oligomerization by SE-HPLC and degradation by SDS-PAGE (see FIGS. 7 to 9). Prior to the study the sample concentration was adjusted to 1 g/L and t0 time points were determined. The monomer content was quantified by separation of the samples on a Shodex KW-402.5-4F (Showa Denko) and evaluation of the resulting chromatograms. For the calculation of the relative percentage of protein monomer the area of the monomeric peak was divided by the total area of peaks that could not be attributed to the sample matrix. The protein degradation was assessed by SDS-PAGE analysis with Any kD Mini-Protean TGX gels (Bio-Rad Laboratories) and stained with Coomassie brilliant blue. The protein concentration was monitored at the different time points by UV-Vis spectroscopy with an Infinity reader M200 Pro equipped with Nanoquant plate (Tecan Group Ltd.).

Example 4: Thermal Unfolding

The midpoint of transition for the thermal unfolding of the tested constructs was determined by Differential Scanning Fluorimetry (DSF), essentially as described by Niesen (Niesen et al., Nat Protoc. 2 (2007) 2212-21). The DSF assay is performed in a qPCR machine (e.g. MX3005p, Agilent Technologies). The samples were diluted in buffer (citrate-phosphate pH 6.4, 0.25 M NaCl) containing a final concentration of 5×SYPRO orange in a total volume of 25 µL. Samples were measured in triplicates and a temperature ramp from 25-96° C. programmed. The fluorescence signal was acquired and the raw data was analyzed with the GraphPad Prism (GraphPad Software Inc.).

Example 5: Affinity Determination

Binding affinities of individual target binding domains in the single-chain Fv (scFv) format as well as of the purified hetero-dimeric tetra-specific constructs to recombinant target proteins human IL-5 receptor (IL5R), human IL-23 receptor ECD (IL23R), human CD3 gamma-epsilon single-chain (CD3) were measured by surface plasmon resonance (SPR) using a MASS-1 SPR instrument (Sierra Sensors). For affinity measurements (done in HEPES running buffer: 0.01 M HEPES, 0.15 M NaCl, 0.05% Tween) human hetero-dimeric single-chain CD3γδ extracellular domain (produced in-house), human IL5R (R&D Systems), human IL23R (Trenzyme) and human TNF (Peprotech), target proteins were immobilized at 100-250 RUs using buffer systems optimized for each individual target, on a sensor chip (SPR-2 Affinity Sensor High Capacity Amine, Sierra Sensors) using a standard amine-coupling procedure. For human TNF-alpha (TNF) a standard amine sensor was used. Two-fold serial dilutions of purified hetero-dimeric tetra-specific constructs ranging from 90 to 0.703 nM were injected into the flow cells for 3 min (20 µl/min) and dissociation was allowed to proceed for 720 sec. After each injection cycle, surfaces were regenerated with a 45 second injection of 10 mM Glycine-HCl pH 1.5. Affinities were calculated by fitting sensograms of at least six concentrations, such that the average $Chi^2$ is below 10% or $R_{max}$. For TNF, no serial dilutions but only single concentration measurements at 90 nM were performed. Data is double-subtracted (reference channel and control cycle was subtracted).

Affinities of hetero-dimeric tetra-specific constructs to each of the four targets were generally very similar to the affinities of the individual binding domains (scFvs) used in the tetra-specific format, including those CDRs whose immune reactivity is putatively dependent upon proper dimerization (i.e., those displayed by the dimer-forming Fvs targeting TNFα and CD3ε, respectively). This demonstrates full functionality of each variable domain in the tetra-specific constructs and confirms correct assembly of the cognate variable domain pairs.

Additionally, each of the three multispecifics was capable of binding all four target antigens simultaneously, seemingly irrespective of the order of antigen-encounter, as demonstrated by SPR analysis of immobilized MATCH protein (FIG. 11).

It is important to acknowledge that while these data suggest proper inter-MATCH chain assembly, they do not necessarily indicate the absence of non-cognate variable domain associations, specifically the "inverted" pairing of MATCH chains that would produce chimeric CDR sets. It has been suggested that CDR sets influence the efficiency of VL-VH pairing, and our SE-HPLC, SDS-PAGE and SPR data would appear to suggest that cognate pairing of MATCH chains is highly favored. However, in an attempt to assess the degree of MATCH chain inverted pairing, we performed a SE-HPLC analysis of antibody and antibody-antigen complexes after incubation of the MATCH proteins with the molar equivalent of trimeric TNFα (i.e., 3-fold excess TNFα epitope). When applying this method of analysis to the parental anti-TNFα scFv (data not shown), SE-HPLC traces showed discrete peaks consistent with three distinct antibody-antigen complex populations, reflecting the disparate size of 1-, 2- and 3-times scFv:TNFα complexes. Additionally, a peak that was consistent with the presence of residual, non-complexed TNFα in solution was observed, whereas non-complexed scFv was completely absent from solution, thus validating the application of this method to identify "inactive" anti-TNFα antibody.

Separation of MATCH protein and MATCH-antigen complexes was less efficient due to the larger molecular weight of the multispecific molecules. However, our results (FIG. 12) also clearly revealed the presence of three MATCH-TNFα complex populations and residual non-complexed TNFα. Additionally, "shouldering" of the 1×MATCH:TNFα complex peak suggested the presence of inactive, but dimeric, MATCH protein. To estimate the proportion of inactive MATCH protein in solution, the peaks were deconvoluted using PeakFit v.1.2 software, assuming a Gaussian distribution for each peak and plotted to optimize goodness-of-fit (FIG. 12). This analysis estimated the proportion of inactive MATCH protein to be between 4.7 and 11.4% (PRO357<PRO356<PRO355) of total MATCH protein content, supporting that proper dimerization of MATCH chains is highly favored, particularly in the antiparallel format.

TABLE 1

Constructs

| Protein chains | | Linker 1 | Core domain Fv 1 | Linker 2 | Core domain Fv 2 | Linker 3 |
|---|---|---|---|---|---|---|
| 1 | scFv (αIL23R) | GGGGSGGGGS (SEQ ID NO: 1) | VL (αTNFa) | GGSGGS (SEQ ID NO: 3) | VL (αCD3) | |
| 2 | scFv (αIL5R) | GGGGSGGGGS (SEQ ID NO: 1) | VH (αCD3) | GGSGGS (SEQ ID NO: 3) | VH (αTNFa) | |
| 3 | scFv (αIL23R) | GGGGSGGGGS (SEQ ID NO: 1) | VL (αTNFa) | GGSGGS (SEQ ID NO: 3) | VL (αCD3) | GSC |
| 4 | scFv (αIL5R) | GGGGSGGGGS (SEQ ID NO: 1) | VH (αCD3) | GGSGGS (SEQ ID NO: 3) | VH (αTNFa) | GSC |
| 5 | | | VL (αTNFa) | GGSGGS (SEQ ID NO: 3) | VL (αCD3) | |
| 6 | | | VL (αTNFa) | GGSGGS (SEQ ID NO: 3) | VL (αCD3) | GSC |
| 7 | | | VH (αCD3) | GGGSGGGS (SEQ ID NO: 4) | VH (αTNFa) | GGGGSGGGGS (SEQ ID NO: 1) scFv (αIL5R) |
| 8 | | | VL (αTNFa) | GGSGGS (SEQ ID NO: 3) | VL (αCD3) | |
| 9 | scFv (αIL23R) | GGGGSGGGGS GGGGS (SEQ ID NO: 2) | VL (αTNFa) | GGGGSGGG GSGGGGS (SEQ ID NO: 2) | VL (αCD3) | |
| 10 | scFv (αIL5R) | GGGGSGGGGS GGGGS (SEQ ID NO: 2) | VH (αCD3) | GGGGSGGG GSGGGGS (SEQ ID NO: 2) | VH (αTNFa) | |
| 11 | | | VL (αTNFa) | GGGGSGGG GSGGGGS (SEQ ID NO: 2) | VL (αCD3) | |

TABLE 2

Multispecific format assemblies

Figure 2:
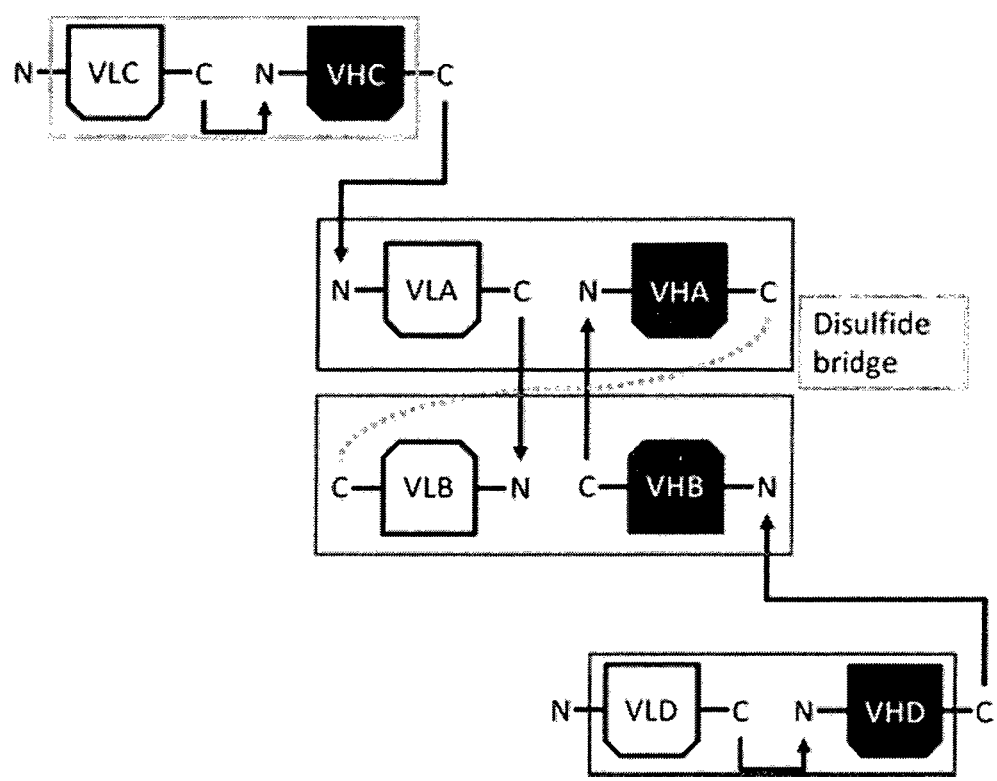
FIG. 2 shows a schematic representation of Assembly 3 (see Example 1).

| Protein ID (Numab) | Assembly | Protein chain 1 | Protein chain 2 |
|---|---|---|---|
| PRO356 | 1 (see FIG. 1) | 1 | 2 |
| PRO469 | 2 | 1 | 5 |
| PRO357 | 3 (see FIG. 2) | 3 | 4 |
| PRO470 | 4 | 4 | 6 |
| PRO358 | 5 (see FIG. 3) | 1 | 7 |
| PRO471 | 6 | 5 | 7 |
| PRO355 | 7 (see FIG. 4) | 9 | 10 |
| PRO468 | 8 | 10 | 11 |

TABLE 3

Size exclusion chromatograms after 1-step purification

| Protein ID (internal) | Assembly ID | Monomer content | FIG. |
|---|---|---|---|
| PRO356 | Assembly 1 | 93.9 | 5A |
| PRO357 | Assembly 3 | 94.4 | 5B |
| PRO358 | Assembly 5 | 93.9 | 5C |
| PRO355 | Assembly 7 | 90.4 | 5D |

TABLE 4

Midpoint of unfolding for the proteins determined by differential scanning fluorimetry

| Protein ID (internal) | Assembly ID | Tm [° C.] |
|---|---|---|
| PRO356 | 1 | 67.99 |
| PRO469 | 2 | 67.24 |
| PRO357 | 3 | 71.27 |
| PRO470 | 4 | 70.34 |
| PRO358 | 5 | 68.51 |
| PRO471 | 6 | 67.98 |
| PRO355 | 7 | 67.33 |
| PRO468 | 8 | 66.67 |

TABLE 5

Affinity of hetero-dimeric tetra-specific constructs

| Protein ID | Affinity to IL5R [M] | Affinity to CD3 M] | Affinity to IL23R [M] | Affinity to TNF [M] |
|---|---|---|---|---|
| scFvs | 2.32E−10 | 8.57E−09 | 1.50E−10 | 2.02E−10 |
| PRO355 | 1.03E−10 | 2.01E−08 | 6.54E−10 | 3.30E−10 |
| PRO356 | 1.26E−10 | 7.14E−09 | 3.41E−10 | 2.01E−10 |
| PRO357 | 1.28E−10 | 6.69E−09 | 3.58E−10 | 1.81E−10 |
| PRO358 | 2.12E−10 | 5.60E−09 | 4.14E−10 | 2.11E−10 |

The invention claimed is:

1. A hetero-dimeric protein comprising a first and a second single-chain protein,
wherein said first single-chain protein comprises a first amino acid sequence consisting of (from the N- to the C-terminus):
(ia) a first VL domain;
(iia) a first polypeptide linker and
(iiia) a second VL domain, and
wherein said second single-chain protein comprises a second amino acid sequence consisting of (from the N- to the C-terminus):
(ib) a first VH domain;
(iib) a second polypeptide linker and
(iiib) a second VH domain, and
wherein said first VL domain forms a first cognate pair of variable domains with specificity to a first target antigen with either said first or said second VH domain, and said second VL domain forms a second cognate pair of variable domains with specificity to a second target antigen with the other of said VH domains, and wherein at least one of said first or said second single-chain protein further comprises:
(iv) a third functional domain that is fused via a third polypeptide linker to said first or said second amino acid sequence;
(v) at least one additional domain as a fourth functional domain that is fused via a fourth polypeptide linker to said first or said second amino acid sequence, so that said hetero-dimeric protein is at least tetraspecific; and
wherein said hetero-dimeric protein does not comprise (i) a cognate pair of a first and a second immunoglobulin constant domain, wherein said first immunoglobulin constant domain is comprised in said first single-chain protein and wherein said second immunoglobulin constant domain is comprised in said second single-chain protein, and wherein said hetero-dimeric protein does not comprise (ii) any further pair of heteroassociation domains, in which one heteroassociation domain of said further pair of heteroassociation domains is located on the first single-chain protein, and the other heteroassociation domain is located on the second single-chain protein, other than said first and second cognate pairs of variable domains,
wherein at least one of said VL and/or VH domains comprises human framework regions, wherein at least one of said VL domains comprises (i) human Vκ framework regions I to III; (ii) CDR domains CDR1, CDR2 and CDR3; and (iii) a framework region IV, which is a human Vλ germ line sequence for framework region IV.

2. The hetero-dimeric protein of claim 1, further comprising
(vi) a fifth functional domain that is fused via a fifth polypeptide linker to said first and said second amino acid sequence; or
(vi) a fifth and a sixth functional domain that are fused via a fifth and a sixth polypeptide linker, respectively, to said first and said second amino acid sequence.

3. The hetero-dimeric protein of claim 1, wherein said first polypeptide linker consists of from 5 to 20 amino acid residues.

4. The hetero-dimeric protein of claim 1, wherein (a) said first VL domain (ia) and said first VH domain (ib) form a first cognate pair of variable domains with specificity to a first target antigen, and said second VL domain (iia) and said second VH domain (iib) form a second cognate pair of variable domains with specificity to a second target antigen; or (b) said first VL domain (ia) and said second VH domain (iib) form a first cognate pair of variable domains with specificity to a first target antigen, and said second VL domain (iia) and said first VH domain (ib) form a second cognate pair of variable domains with specificity to a second target antigen.

5. The hetero-dimeric protein of claim 1, wherein said third and/or fourth functional domains are independently selected from the list of: binding domains, toxins, enzymes, hormones, signaling proteins, and albumins; particularly wherein said third and/or fourth functional domains are independently selected from binding domains; particularly wherein said binding domains are independently selected from the list of: antibody-based binding domains, particularly scFv fragments, Fab fragments and single antibody variable domains, and binding domains based on alternative scaffolds, particularly ankyrin-based domains, fynomers, avimers, anticalins and binding sites being built into constant regions of antibodies.

6. The hetero-dimeric protein of claim 1, wherein at least one of said VL and/or VH domains comprises CDR regions derived from a parental rabbit antibody.

7. The hetero-dimeric protein of claim 1, wherein the cognate pair of one of said first and said second VL and VH domains is specific for an antigen selected from the list of: a cancer target; and a target present on immune effector cells.

8. A nucleic acid sequence or two nucleic acid sequences encoding the first and the second single-chain proteins of the hetero-dimeric protein of claim 1.

9. A vector or two vectors comprising the nucleic acid sequence or the two nucleic acid sequences of claim 8.

10. A host cell or host cells comprising the vector or the two vectors of claim 9.

11. A method for producing the hetero-dimeric protein of claim 1, or the first and the second single-chain proteins of said hetero-dimeric protein, comprising (i) providing a nucleic acid sequence or two nucleic acid sequences encoding the first and the second single-chain proteins of the hetero-dimeric protein of claim 1, or a vector or two vectors comprising said nucleic acid sequence or nucleic acid sequences, expressing said nucleic acid sequence or nucleic acid sequences, or said vector or vectors, and collecting said hetero-dimeric protein, or (ii) providing a host cell or host cells comprising said vector or vectors, culturing said host cell or said host cells; and collecting said first and second single-chain proteins, or said hetero-dimeric protein, from the cell culture.

12. A pharmaceutical composition comprising the hetero-dimeric protein of claim 1 and a pharmaceutically acceptable carrier.

13. The hetero-dimeric protein of claim 1 for use in the treatment of a disease, wherein at least one of said cognate pairs of VL and VH domains, or of said third or fourth functional domain is able to specifically interact with a target of therapeutic relevance in the disease.

14. The hetero-dimeric protein of claim 7, wherein said antigen is CD3.

15. The hetero-dimeric protein of claim 1 for use in the treatment of a human disease, wherein at least one of said cognate pairs of VL and VH domains, or of said third or fourth functional domain is able to specifically interact with a target of therapeutic relevance in the disease.

16. The hetero-dimeric protein of claim 1 for use in the treatment of a human disease selected from cancer, an inflammatory and an autoimmune disease, wherein at least one of said cognate pairs of VL and VH domains, or of said third or fourth functional domain is able to specifically interact with a target of therapeutic relevance in the disease.

17. The hetero-dimeric protein of claim 1, wherein said first polypeptide linker consists of from 6 to 15 amino acid residues.

* * * * *